United States Patent
Matsumoto

(10) Patent No.: US 8,690,758 B2
(45) Date of Patent: Apr. 8, 2014

(54) FLUORESCENT ENDOSCOPE APPARATUS

(75) Inventor: Shinya Matsumoto, Machida (JP)

(73) Assignee: Olympus Corporation, Tokyo (JP)

( * ) Notice: Subject to any disclaimer, the term of this patent is extended or adjusted under 35 U.S.C. 154(b) by 280 days.

(21) Appl. No.: 13/073,154

(22) Filed: Mar. 28, 2011

(65) Prior Publication Data

US 2011/0282143 A1 Nov. 17, 2011

(30) Foreign Application Priority Data

Mar. 29, 2010 (JP) ................................ 2010-075676

(51) Int. Cl.
*A61B 1/04* (2006.01)
*A61B 1/06* (2006.01)
*A61B 5/00* (2006.01)

(52) U.S. Cl.
USPC ............ 600/109; 600/180; 600/317; 600/160

(58) Field of Classification Search
USPC ............ 600/109, 476, 180, 317, 178, 160, 3; 607/88; 348/68, 77, 65, 45; 604/20
See application file for complete search history.

(56) References Cited

U.S. PATENT DOCUMENTS

| | | | | |
|---|---|---|---|---|
| 7,956,311 B2 * | 6/2011 | Ohno | | 250/201.1 |
| 8,188,446 B2 * | 5/2012 | Ohno | | 250/461.1 |
| 8,313,426 B2 * | 11/2012 | Nakaoka et al. | | 600/160 |
| 2001/0055424 A1 | 12/2001 | Publicover | | 382/195 |
| 2003/0001104 A1 * | 1/2003 | Sendai et al. | | 250/458.1 |
| 2007/0013771 A1 * | 1/2007 | Imaizumi et al. | | 348/74 |
| 2007/0016077 A1 * | 1/2007 | Nakaoka et al. | | 600/476 |
| 2007/0213588 A1 * | 9/2007 | Morishita et al. | | 600/156 |
| 2007/0213593 A1 * | 9/2007 | Nakaoka | | 600/181 |
| 2007/0273888 A1 * | 11/2007 | Kamihara | | 356/454 |
| 2009/0021739 A1 * | 1/2009 | Tsujita et al. | | 356/407 |
| 2010/0016669 A1 * | 1/2010 | Takaoka et al. | | 600/160 |
| 2010/0044550 A1 * | 2/2010 | Ohno | | 250/201.1 |
| 2010/0067002 A1 * | 3/2010 | Ishii | | 356/317 |
| 2010/0084563 A1 * | 4/2010 | Ohno | | 250/363.01 |
| 2010/0094136 A1 * | 4/2010 | Nakaoka et al. | | 600/477 |
| 2010/0234739 A1 * | 9/2010 | Nakaoka et al. | | 600/476 |
| 2011/0009702 A1 * | 1/2011 | Morishita et al. | | 600/178 |
| 2011/0068278 A1 * | 3/2011 | Morishita et al. | | 250/458.1 |
| 2011/0080582 A1 * | 4/2011 | Kamihara | | 356/326 |
| 2011/0160077 A1 * | 6/2011 | Chaisson et al. | | 506/9 |
| 2011/0243414 A1 * | 10/2011 | Yamamoto et al. | | 382/131 |

FOREIGN PATENT DOCUMENTS

JP 2004-000478 1/2004

* cited by examiner

*Primary Examiner* — John P Leubecker
*Assistant Examiner* — Ronald D Colque
(74) *Attorney, Agent, or Firm* — Scully, Scott, Murphy & Presser, P.C.

(57) ABSTRACT

A fluorescent endoscope apparatus includes an excitation light irradiation system for irradiating a living body with excitation light, a wavelength-selective transmission member which transmits light from the living body in a wavelength-selective manner, a photodetector which photoelectrically converts the selected and transmitted light, a wavelength selection control section which controls the wavelength-selective transmission member, to make it select and transmit light in a plurality of fluorescence detection wavelength regions and light in spectrum acquisition wavelength regions in a predetermined wavelength range that includes at least one of the fluorescence detection wavelength regions, a fluorescence image synthesizer for synthesizing images in the fluorescence detection wavelength regions, a display device for displaying the synthesized image, and an intensity distribution acquisition section which acquires the intensity distribution of light in the predetermined wavelength range.

16 Claims, 14 Drawing Sheets

FIG. 8
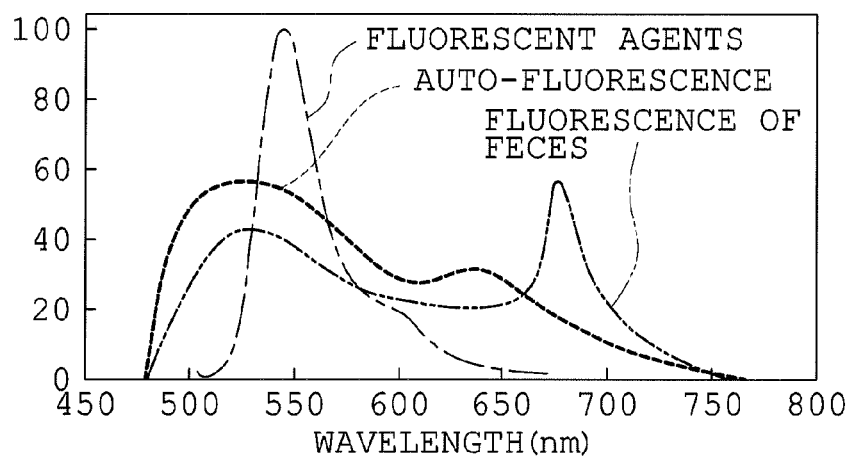
FIG. 9A
EXAMPLE)
THREE WAVELENGTHS
DISPLAY IN MONITOR
(MOVING IMAGE)
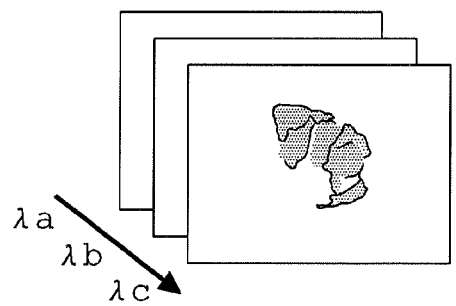
FIG. 9B
EXAMPLE)
CAREFULLY EXAMINED SPECTRAL
IMAGE IS OBTAINED IN BACK
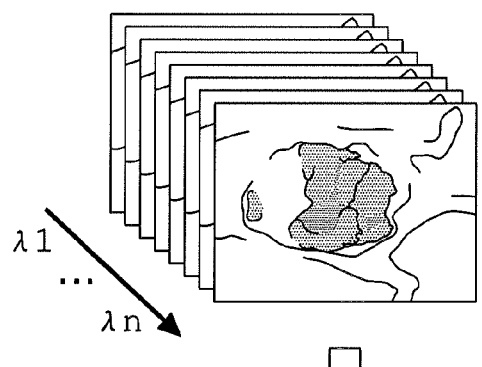
SPECTRUM IS OBTAINED AT
EACH IMAGE POSITION
(PICTURE ELEMENT)
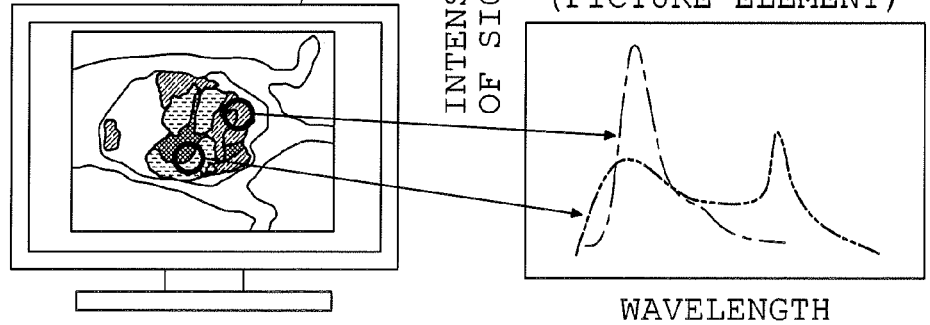

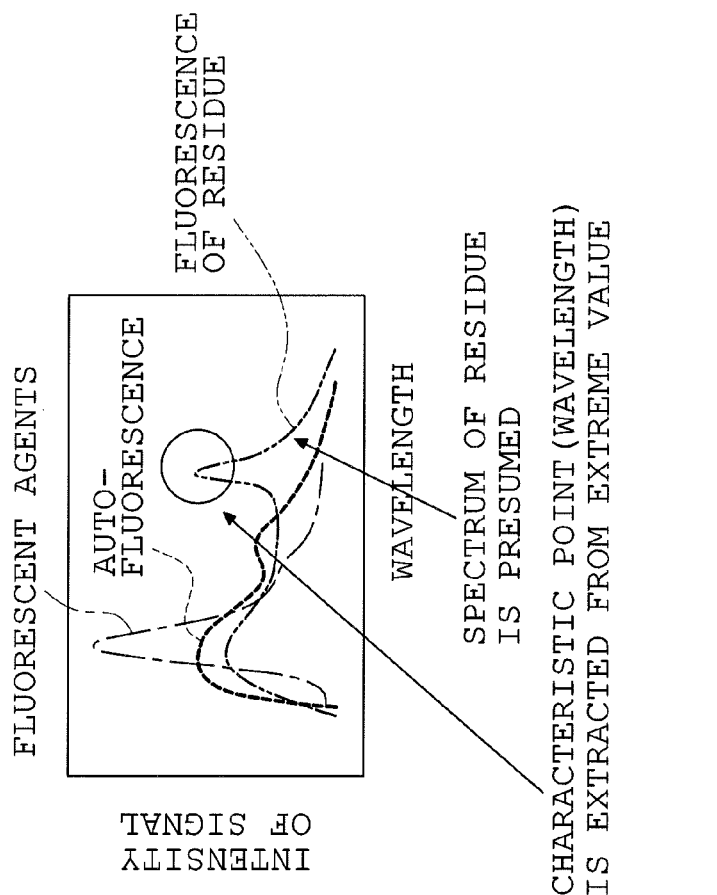
FIG. 10C  Spectrum of each component separated (spectrum assumption) unknown component (residue) can be presumed from known component
FIG. 10B  Detected spectrum
FIG. 10A  Each spectrum of pigment and auto-fluorescence derived from living body, in which it is already known to include

FOR OBSERVATION OF MOVING IMAGE

FOR SPECTRAL ANALYSIS

FOR OBSERVATION OF MOVING IMAGE

PICTURE ELEMENT AREA SPECIFYING MEANS

FOR OBSERVATION OF MOVING IMAGE

FOR SPECTRAL ANALYSIS

FOR OBSERVATION OF MOVING IMAGE

FOR SPECTRAL ANALYSIS

FIG.17
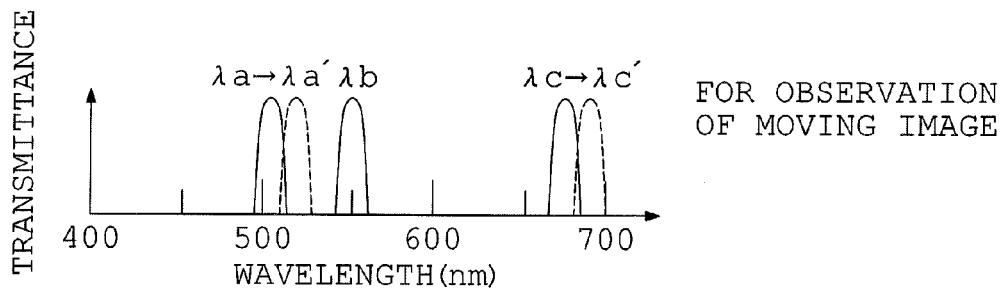
FOR OBSERVATION OF MOVING IMAGE
FIG.18A
FIG.18B
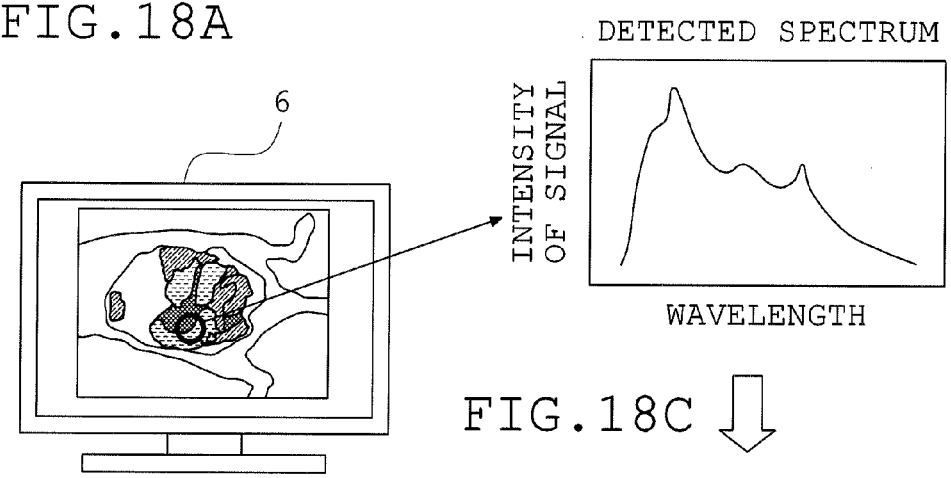
DETECTED SPECTRUM
FIG.18C ⇩
SPECTRUM OF EACH COMPONENT
SEPARATED (SPECTRUM ASSUMPTION)
UNKNOWN COMPONENT (RESIDUE) CAN
BE PRESUMED FROM KNOWN COMPONENT
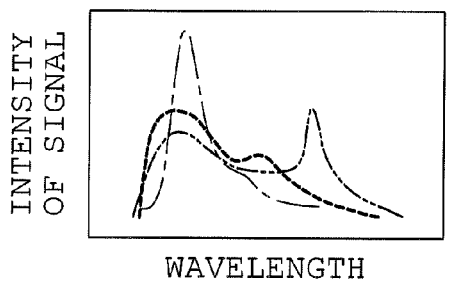

FOR OBSERVATION OF MOVING IMAGE

FOR SPECTRAL ANALYSIS

FLUORESCENT ENDOSCOPE APPARATUS

This application claims benefits of Japanese Patent Application No. 2010-075676 filed in Japan on Mar. 29, 2010, the contents of which are hereby incorporated by reference.

BACKGROUND OF THE INVENTION

1. Field of the Invention

This invention relates to a fluorescent endoscope apparatus of detecting a fluorescence spectrum resulting from a biological tissue in order to observe the biological tissue.

2. Description of the Related Art

Conventionally, this kind of fluorescent endoscope apparatus is disclosed, for example, in Japanese Patent No. 4109133.

Now, a component which causes variations in the fluorescent spectra of a labeled fluorescent agent and auto-fluorescence, for example, to have a bad influence upon a decision on lesion tissue (for example, residue emitting fluorescence or the like) exists in a living body. Also, the fluorescent spectra obtained from a living body make a difference among individuals.

Accordingly, the fluorescent endoscope apparatus which is described in Japanese Patent No. 4109133 is formed in such a way that: after the information about the distributions of a plurality of feature quantities is acquired on the basis of the fluorescence information about a clean biological tissue to which residues or the like do not adhere, in advance, a plurality of feature quantities are acquired on the basis of the fluorescence information which is obtained from an area to be measured; and a decision whether the area to be measured is a clean tissue to which residues or the like do not adhere or not is made on the basis of the acquired feature quantities and the information about the distributions of the feature quantities that was acquired in advance on the basis of the fluorescence information about the clean biological tissue to which residues or the like do not adhere. As a result, the fluorescent endoscope apparatus which is described in Japanese Patent No. 4109133 makes it possible to improve the reliability of the result of a decision on tissue characterization.

SUMMARY OF THE INVENTION

A fluorescent endoscope apparatus according to the present invention is characterized in that the fluorescent endoscope apparatus comprises: an excitation light irradiation means which irradiates excitation light for exciting a plural kind of fluorescent agents that exist in an observation area of a living body, to the observation area; a wavelength selection and transmission means which selects and transmits light of a predetermined wavelength that enters from the observation area of the living body; a photo detector means by which the light that has been selected and transmitted by the wavelength selection and transmission means is photoelectrically converted; a wavelength selection control means which controls the wavelength selection and transmission means so that the wavelength selection and transmission means selects and transmits light in fluorescence detection wavelength regions that correspond to the plural kind of fluorescence emitting from the plural kind of the fluorescent agents respectively, and light in spectrum acquisition wavelength regions that adjoin each other in turn with a predetermined wavelength width in a predetermined wavelength range that includes a fluorescence detection wavelength region corresponding to at least one kind of fluorescence in the plural kind of fluorescence; a fluorescent image compounding means which compounds images of the lights in the fluorescence detection wavelength regions that has been selected and transmitted by the wavelength selection and transmission means and that has been photoelectrically converted by the photo detector means; an image display means which displays the images that have been synthesized at least by the fluorescent image compounding means; and an intensity distribution obtaining means which acquires the intensity distribution of lights in the predetermined wavelength range by the use of the images of the lights in the respective spectrum acquisition wavelength regions in the predetermined wavelength range that has been selected and transmitted by the wavelength selection and transmission means and that has been photoelectrically converted by the photo detector means.

Also, in a fluorescent endoscope apparatus of the present invention, it is preferred that the fluorescent endoscope apparatus comprises a wavelength selection control adjusting means which adjusts control of the wavelength selection and transmission means selecting fluorescence detection wavelength region and transmitting the light in the selected wavelength region by the wavelength selection control means, in such a way that a fluorescence detection wavelength region corresponding to at least one kind of fluorescence which is selected and transmitted by the wavelength selection and transmission means is shifted to a peak wavelength region in the intensity distribution of the light in the predetermined wavelength range that includes the fluorescence detection wavelength region, the intensity distribution of the light being acquired by the intensity distribution obtaining means.

Also, in a fluorescent endoscope apparatus of the present invention, it is preferred that the wavelength selection control means controls the wavelength selection and transmission means in such a way that, after the wavelength selection and transmission means selects and transmits light in all of the fluorescence detection wavelength regions, the wavelength selection and transmission means selects and transmits light in all of the spectrum acquisition wavelength regions.

Also, in a fluorescent endoscope apparatus of the present invention, it is preferred that the wavelength selection control means controls the wavelength selection and transmission means in such a way that: after the wavelength selection and transmission means selects and transmits light in all of the fluorescence detection wavelength regions, the wavelength selection and transmission means selects and transmits light in one of the spectrum acquisition wavelength regions; and a sequence of these processes is repeated until light in all of the spectrum acquisition wavelength regions is selected and transmitted.

Also, in a fluorescent endoscope apparatus of the present invention, it is preferred that: the wavelength selection control means has a first control mode in which the wavelength selection control means controls the wavelength selection and transmission means in such a way that the wavelength selection and transmission means selects and transmits light in all of the fluorescence detection wavelength regions, and a second control mode in which the wavelength selection control means controls the wavelength selection and transmission means in such a way that the wavelength selection and transmission means selects and transmits light in all of the spectrum acquisition wavelength regions; and the wavelength selection control means can be driven through a selection of one of the first and second control modes by a manual operation.

Also, in a fluorescent endoscope apparatus of the present invention, it is preferred that: the wavelength selection control means has the first control mode in which the wavelength selection control means controls the wavelength selection and transmission means in such a way that the wavelength selection and transmission means selects and transmits light in all of the fluorescence detection wavelength regions, and a third control mode in which the wavelength selection control means controls the wavelength selection and transmission means in such a way that, after the wavelength selection and transmission means selects and transmits light in all of the fluorescence detection wavelength regions, the wavelength selection and transmission means selects and transmits light in one of the spectrum acquisition wavelength regions, and a sequence of these processes is repeated until light in all of the spectrum acquisition wavelength regions is selected and transmitted; and the wavelength selection control means can be driven through a selection of one of the first and third control modes by a manual operation.

Also, in a fluorescent endoscope apparatus of the present invention, it is preferred that the fluorescent endoscope apparatus further comprises a pixel area specifying means which specifies a desired pixel area on which the intensity distribution of light in the predetermined wavelength range is acquired by the intensity distribution obtaining means, and the light intensity distribution obtaining means acquires the intensity distribution of light in the predetermined wavelength range relative to a pixel area which is specified by the pixel area specifying means.

Also, in a fluorescent endoscope apparatus of the present invention, it is preferred that the wavelength selection control adjusting means automatically makes an adjustment to control of the wavelength selection and transmission means selecting fluorescence detection wavelength region and transmitting light in the selected wavelength region by the wavelength selection control means.

Also, in a fluorescent endoscope apparatus of the present invention, it is preferred that the wavelength selection control adjusting means manually makes an adjustment to control of the wavelength selection and transmission means selecting fluorescence detection wavelength region and transmitting light in the selected wavelength region by the wavelength selection control means.

Also, in a fluorescent endoscope apparatus of the present invention, it is preferred that: the fluorescent endoscope apparatus further comprises a moving amount detecting means which detects a moving amount in the observation area by using a change of a fluorescence image which is compounded by the fluorescence image compounding means; the wavelength selection control means has a first control mode in which the wavelength selection control means controls the wavelength selection and transmission means in such a way that the wavelength selection and transmission means selects and transmits light in all of the fluorescence detection wavelength regions, and the second control mode in which the wavelength selection control means controls the wavelength selection and transmission means in such a way that the wavelength selection and transmission means selects and transmits light in all of the spectrum acquisition wavelength regions; and, when a moving amount which is detected by the moving amount detecting means is equal to or smaller than a predetermined value, the wavelength selection control means is driven with the second control mode, and when a moving amount which is detected by the moving amount detecting means is larger than the predetermined value, the wavelength selection control means is driven with the first control mode.

Also, in a fluorescent endoscope apparatus of the present invention, it is preferred that: the fluorescent endoscope apparatus further comprises a moving amount detecting means which detects a moving amount in the observation area by using a change of a fluorescence image which is compounded by the fluorescence image compounding means; the wavelength selection control means has a first control mode in which the wavelength selection control means controls the wavelength selection and transmission means in such a way that the wavelength selection and transmission means selects and transmits light in all of the fluorescence detection wavelength regions, and a third control mode in which the wavelength selection control means controls the wavelength selection and transmission means in such a way that, after the wavelength selection and transmission means selects and transmits light in all of the fluorescence detection wavelength regions, the wavelength selection and transmission means selects and transmits light in one of the spectrum acquisition wavelength regions, and a sequence of these processes is repeated until light in all of the spectrum acquisition wavelength regions is selected and transmitted; and, when a moving amount which is detected by the moving amount detecting means is equal to or smaller than a predetermined value, the wavelength selection control means is driven with the third control mode, and when a moving amount which is detected by the moving amount detecting means is larger than the predetermined value, the wavelength selection control means is driven with the first control mode.

Also, in a fluorescent endoscope apparatus of the present invention, it is preferred that the intensity distribution obtaining means operates when a moving amount which is detected by the moving amount detecting means is equal to or smaller than the predetermined value.

Also, in a fluorescent endoscope apparatus of the present invention, it is preferred that the fluorescent endoscope apparatus further comprises a moving amount detecting means which detects a moving amount in the observation area by using a change of a fluorescence image which is compounded by the fluorescence image compounding means, and the intensity distribution obtaining means operates when a moving amount which is detected by the moving amount detecting means is equal to or smaller than the predetermined value.

Also, in a fluorescent endoscope apparatus of the present invention, it is preferred that the intensity distribution obtaining means further includes a targeted wavelength region setting means which can set the predetermined wavelength range that becomes a target range for acquiring intensity distribution.

Also, in a fluorescent endoscope apparatus of the present invention, it is preferred that the fluorescent endoscope apparatus further comprises a spectrum division means which divides a specific spectrum by using the intensity distribution of light in the predetermined wavelength range which is acquired by the intensity distribution obtaining means.

Also, in a fluorescent endoscope apparatus of the present invention, it is preferred that the image display means displays the intensity distribution of light in the predetermined wavelength range which is acquired by the intensity distribution obtaining means, together with an image which is compounded by the fluorescent image compounding means.

The present invention is capable of offering a fluorescent endoscope apparatus which makes it possible to acquire a fluorescence spectrum for detecting variations in fluorescence spectrum due to residue, difference among individuals, or the like, in order to select and adjust a suitable wavelength region for detecting fluorescence emitting from lesion or residue in observation of a biological tissue, regardless of the presence or absence of a factor in variations in fluorescence spectrum due to residue, difference among individuals, or the like.

These and other features and advantages of the present invention will become apparent from the following detailed description of the preferred embodiments when taken in conjunction with accompanying drawings.

BRIEF DESCRIPTION OF THE DRAWINGS

FIG. 2 is a view showing one example of wavelength regions which the wavelength selection and transmission means selects and transmits light in the wavelength regions in the fluorescent endoscope apparatus shown in FIG. 1.

FIG. 3 is an explanatory view showing one example of timing to acquire a spectral image in the fluorescent endoscope apparatus shown in FIG. 1.

FIG. 4 is an explanatory view showing another example of timing to acquire a spectral image in the fluorescent endoscope apparatus shown in FIG. 1.

FIG. 8 is a graph showing the spectral transmittance characteristic of plural kinds of fluorescence which exists in a living body that is an object for observation in the fluorescent endoscope apparatus shown in FIG. 5.

FIG. 9 is an explanatory view showing the relation between an image and a spectrum which are acquired with the fluorescent endoscope apparatus shown in FIG. 5, FIG. 9A is a view showing the images of light in three kinds of fluorescence detection wavelength regions, which are written on respective frame memories for synthesis of fluorescence image, and showing an image into which these images are compounded by the fluorescent image compounding means and which is displayed by the image display means, and FIG. 9B is a graph showing the images of light in spectrum acquisition wavelength regions extending throughout a predetermined wavelength range, which are recorded on a frame memory for acquisition of intensity distribution, and showing a fluorescence spectrum at a predetermined image position, which is acquired through the intensity distribution obtaining means by using these images.

FIG. 10 is an explanatory view conceptually showing a method for dividing a fluorescence spectrum by which is acquired by the intensity distribution obtaining means and in which a plural kind of fluorescence components intermingle with one another, into its respective fluorescence components, FIG. 10A is a graph showing the spectra of autofluorescence originating from a living body and of fluorescence emitting from a fluorescent agent for labeling the living body, which is already known to be contained in the living body in advance, respectively, FIG. 10B is a graph showing one example of a fluorescence spectrum which is acquired by the intensity distribution obtaining means, and FIG. 10C is a graph showing the fluorescence spectrum which is shown in FIG. 10B and is divided into its fluorescence components by the spectrum division means.

FIG. 11 is a view showing one example of wavelength region which the wavelength selection and transmission means selects to transmit light in the wavelength region in fluorescent endoscope apparatus according to the embodiment 1.

FIG. 12 is an explanatory view showing one variation of timing to acquire a spectral image in the fluorescent endoscope apparatus of the embodiment 1.

FIG. 13 is an explanatory view showing a fluorescence image which is displayed by the display means and showing a fluorescence spectrum which is acquired by the intensity distribution obtaining means, in the fluorescent endoscope apparatus of the embodiment 1.

FIG. 14 is a view showing one example of wavelength region which the wavelength selection and transmission means selects and transmits light in the wavelength region in the fluorescent endoscope apparatus according to the embodiment 2.

FIG. 16 is a view showing one example of wavelength region which the wavelength selection and transmission means selects and transmits light in the wavelength region in the fluorescent endoscope apparatus according to the embodiment 3.

FIG. 17 is a view showing one example of fluorescence detection wavelength region which the wavelength selection and transmission means 2 selects and transmits light in the wavelength region in the fluorescent endoscope apparatus according to the embodiment 4, and a showing a state in which two kinds of fluorescence detection wavelength regions are shifted.

FIG. 18 is an explanatory view showing a fluorescence image which is displayed by the image display means, showing a fluorescence spectrum which is acquired by the intensity distribution obtaining means, and showing the fluorescence spectrum which is divided by the spectrum division means, in the fluorescent endoscope apparatus of the embodiment 4, FIG. 18A is a view showing an image into which the images of light in three kinds of fluorescence detection wavelength regions that are written on respective frame memories for synthesis of fluorescence image are compounded by the fluorescent image compounding means and which is displayed by the image display means, FIG. 18B is a graph showing a fluorescence spectrum that is acquired by the intensity distribution obtaining means relative to a pixel area specified through the pixel area specifying means in the image shown in FIG. 18A, and FIG. 18C is a graph showing the fluorescence spectrum shown in FIG. 18B which is divided into its fluorescence components by the spectrum division means.

FIG. 19 is a view showing an example of a method for determining a pixel area which becomes an object for adjustment to the shift to a fluorescence detection wavelength region which the wavelength selection and transmission means selects and transmits light in the wavelength region by control from the wavelength selection control means through the wavelength selection control adjusting means, in the fluorescent endoscope apparatus of the embodiment 6.

FIG. 20 is a view showing one example of wavelength region which the wavelength selection and transmission means selects and transmits light in the wavelength region in the fluorescent endoscope apparatus according to the embodiment 7.

DETAILED DESCRIPTION OF THE PREFERRED EMBODIMENTS

Prior to the description of the embodiments of the present invention, constitutions for the present invention and operation effects caused by the constitutions will be schematically explained.

Figure 1:
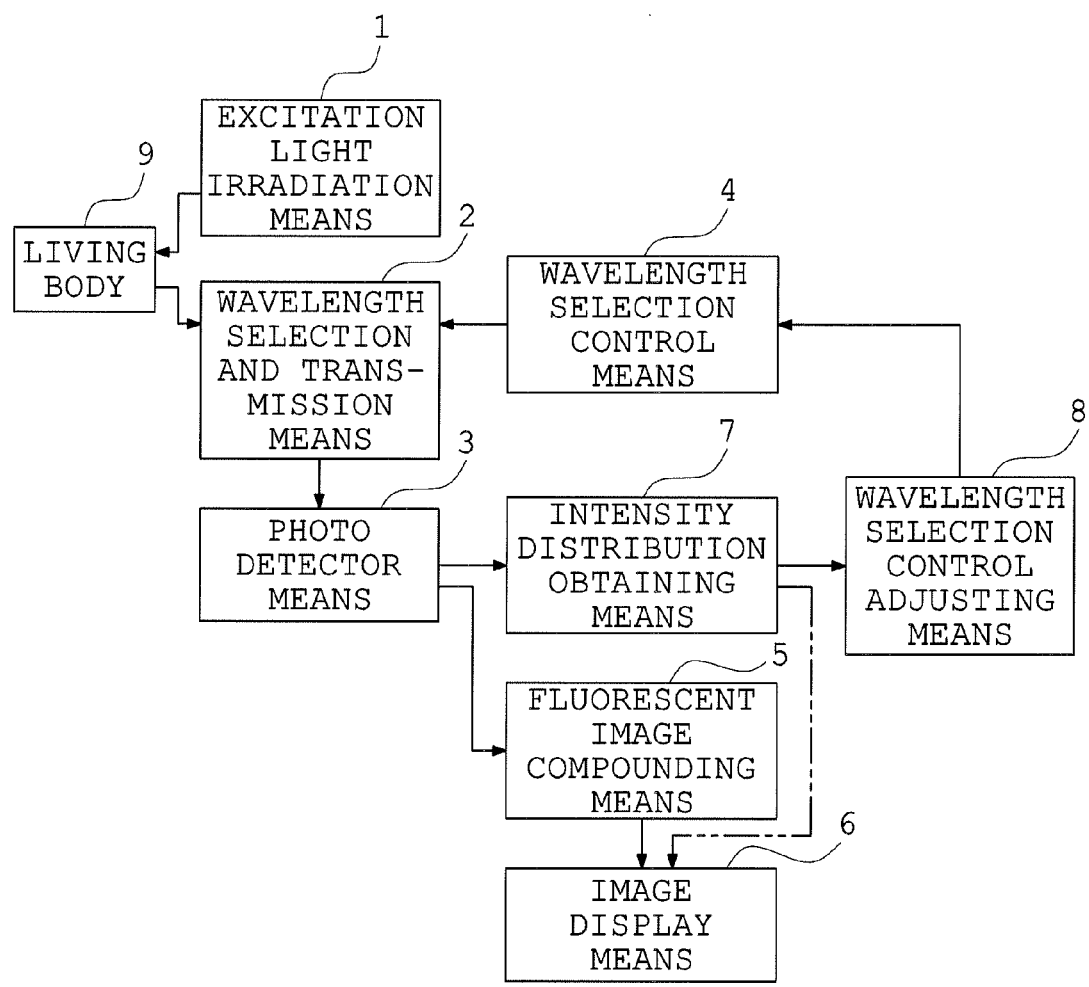
FIG. 1 is a block diagram schematically showing one example of the constitution of a primary part in the whole of a fluorescent endoscope apparatus of the present invention.
Figure 2A:
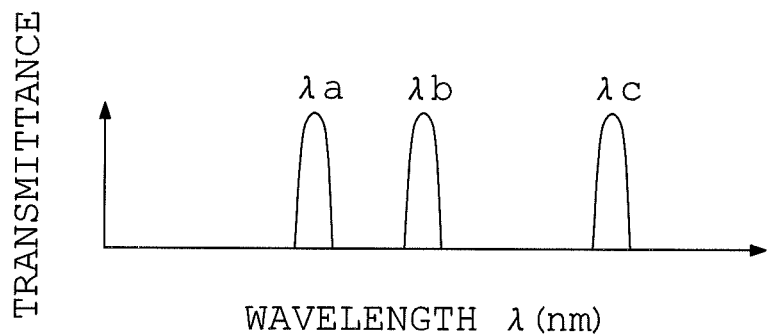
FIG. 2A shows respective fluorescence detection wavelength regions.
Figure 2B:
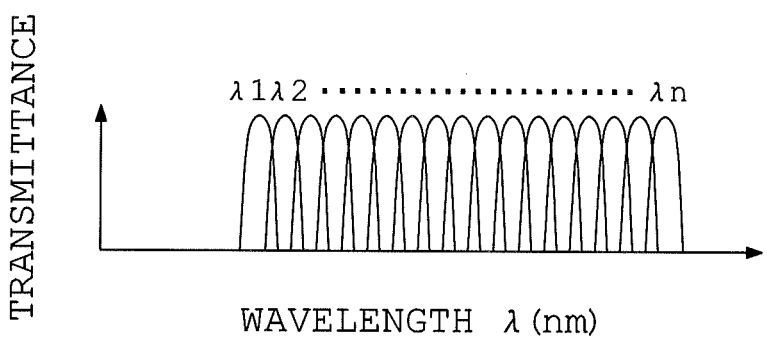
FIG. 2B shows respective spectrum acquisition wavelength regions.
Figure 2C:
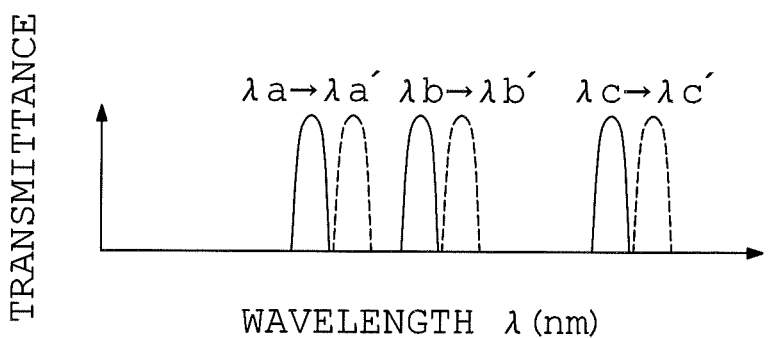
FIG. 2C shows a state in which the respective fluorescence detection wavelength regions are shifted.
Figure 3A:
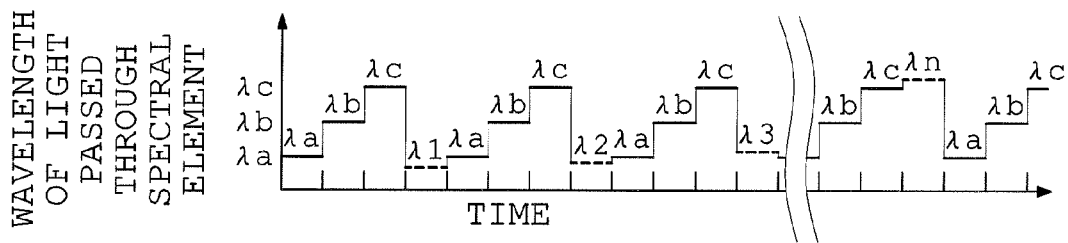
FIG. 3A is a view chronologically showing light in respective wavelength regions which the wavelength selection and transmission means selects and transmits the light in the wavelength regions.
Figure 3B:
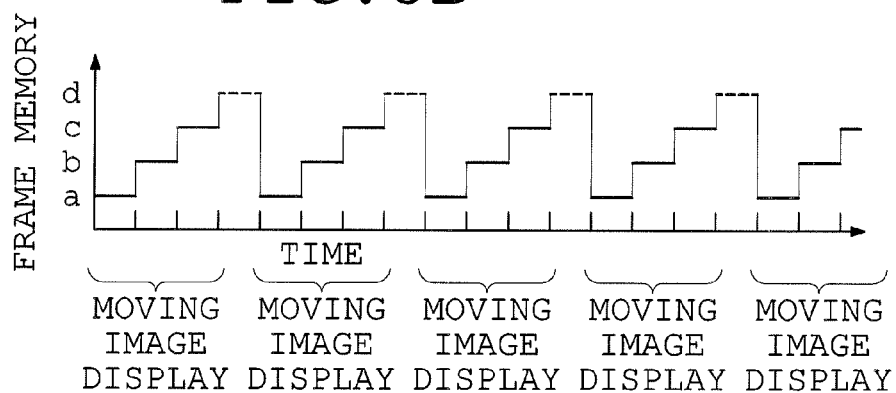
FIG. 3B is a view chronologically showing light in respective wavelength regions which is photoelectrically converted at approximately the same time as FIG. 3A through the photo detector means, to be recorded on respective frame memories.
Figure 4A:
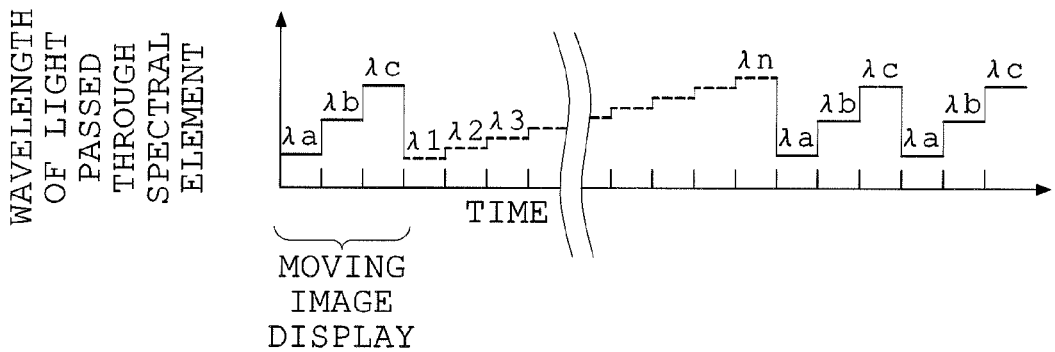
FIG. 4A is a view chronologically showing light in respective wavelength regions which the wavelength selection and transmission means selects and transmits the light in the wavelength regions.
Figure 4B:
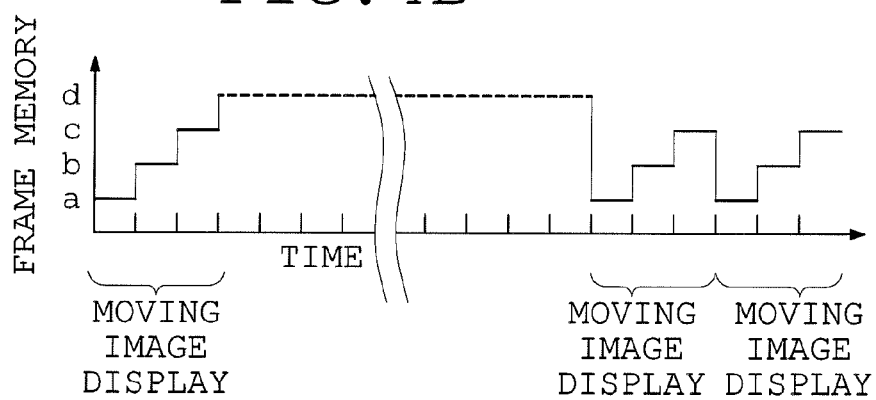
FIG. 4B is a view chronologically showing light in respective wavelength regions which is photoelectrically converted at approximately the same time as FIG. 4A through the photo detector means, to be recorded on respective frame memories.

FIG. 1 is a block diagram schematically showing one example of the constitution of a primary part in the whole of a fluorescent endoscope apparatus of the present invention. FIG. 2 is a view showing one example of wavelength regions which the wavelength selection and transmission means selects and transmits light in the wavelength regions in the fluorescent endoscope apparatus shown in FIG. 1, FIG. 2A is a view showing respective fluorescence detection wavelength regions, FIG. 2B is a view showing respective spectrum acquisition wavelength regions, and FIG. 2C is a view showing a state in which the respective fluorescence detection wavelength regions are shifted. FIG. 3 is an explanatory view showing one example of timing to acquire a spectral image in the fluorescent endoscope apparatus shown in FIG. 1, FIG. 3A is a view chronologically showing light in respective wavelength regions which the wavelength selection and transmission means selects and transmits the light in the wavelength regions, and FIG. 3B is a view chronologically showing light in respective wavelength regions which is photoelectrically converted at approximately the same time as FIG. 3A through the photo detector means, to be recorded on respective frame memories. FIG. 4 is an explanatory view showing another example of timing to acquire a spectral image in the fluorescent endoscope apparatus shown in FIG. 1, FIG. 4A is a view chronologically showing light in respective wavelength regions which the wavelength selection and transmission means selects and transmits the light in the wavelength regions, and FIG. 4B is a view chronologically showing light in respective wavelength regions which is photoelectrically converted at approximately the same time as FIG. 4A through the photo detector means, to be recorded on respective frame memories.

The fluorescent endoscope apparatus which is shown in FIG. 1 comprises an excitation light irradiation means 1, a wavelength selection and transmission means 2, a photo detector means 3, a wavelength selection control means 4, a fluorescent image compounding means 5, an image display means 6, an intensity distribution obtaining means 7, and a wavelength selection control adjusting means 8.

The excitation light irradiation means 1 includes a light source for excitation which is provided for a light source unit that is omitted in the drawings, an illumination optical system which is provided for the top end portion of the endoscope that is omitted in the drawings, and a light guide which connects the light source for excitation and the illumination optical system and is omitted in the drawings, for example. The excitation light irradiation means 1 irradiates to an observation area in a living body 9 excitation light which excites plural kinds of fluorescent agents that exist in the observation area.

The wavelength selection and transmission means 2 is composed of a spectral optical device like etalon which is provided on the optical path of the image pick up optical system that is provided for the top end portion of the endoscope that is omitted in the drawings. The wavelength selection and transmission means 2 selects light in a predetermined wavelength region among light entering from the living body 9, to transmit the light in the predetermined wavelength region. Besides, the image pick up optical system is not only provided with the wavelength selection and transmission means 2, but also provided with an objective optical system, an image forming optical system, an excitation light cut filter, and a photo detector means 3 that is described below, for example.

The photo detector means 3 is composed of an image sensor like CCD which is provided on the optical path of the image pick up optical system that is provided in the top end portion of the endoscope that is omitted in the drawings. The photo detector means 3 photoelectrically converts light which is selected to be transmitted by the wavelength selection and transmission means 2. An image into which the light is photoelectrically converted is written on a frame memory that is provided in a control unit that is omitted in the drawings.

The wavelength selection control means 4 is provided in the control unit that is omitted in the drawings. The wavelength selection control means 4 controls the wavelength selection and transmission means 2 in such a way that the wavelength selection and transmission means 2 selects: light in fluorescence detection wavelength regions $\lambda a$, $\lambda b$, and $\lambda c$ which correspond to plural kinds of fluorescence that emit from plural kinds of fluorescent agents, respectively, as shown in FIG. 2A for example; and light in spectrum acquisition wavelength regions $\lambda 1, \lambda 2, \ldots, \lambda n$ which adjoin each other in turn with a predetermined wavelength width in a predetermined wavelength range that includes a fluorescence detection wavelength region corresponding to at least one kind of fluorescence among the plural kinds of the fluorescence (where, in FIG. 2B, the predetermined wavelength range includes the fluorescence detection wavelength regions $\lambda a$, $\lambda b$, and $\lambda c$ which correspond to all the kinds of the fluorescence), as shown in FIG. 2B for example, to transmit the selected light.

In this case, the wavelength selection control means 4 controls the wavelength selection and transmission means 2 in such a way that: timing with which the wavelength selection and transmission means 2 selects fluorescence detection wavelength region and spectrum acquisition wavelength region to transmit light in the wavelength regions is such that the wavelength selection and transmission means 2 selects light in one spectrum acquisition wavelength region to transmit the light in the spectrum acquisition wavelength region after selecting light in all of the fluorescence detection wavelength regions $\lambda a$, $\lambda b$, and $\lambda c$ to transmit the light in all of the fluorescence detection wavelength regions, as shown in FIG. 3A for example; and a sequence of these processes is repeated until light in all of the spectrum acquisition wavelength regions is selected to be transmitted.

Besides, the above, "light in all of the spectrum acquisition wavelength regions" means "a plural kind of light which adjoin each other in turn with a predetermined wavelength width in a predetermined wavelength range that includes a fluorescence detection wavelength region corresponding to at least one kind of fluorescence among the plural kind of the fluorescence", as described above.

Or, for example, as shown in FIG. 4B, the wavelength selection control means 4 may control the wavelength selection and transmission means 2 in such a way that the wavelength selection and transmission means 2 selects and transmits light in all of the spectrum acquisition wavelength regions $\lambda 1, \lambda 2, \ldots, \lambda n$ after light in all of the fluorescence detection wavelength regions $\lambda a$, $\lambda b$, and $\lambda c$ has been selected and transmitted.

In this case, the above, "light in all of the spectrum acquisition wavelength regions" means "a plural kind of light which adjoin each other in turn with a predetermined wavelength width in a predetermined wavelength range that includes a fluorescence detection wavelength region corresponding to at least one kind of fluorescence among the plural kind of the fluorescence", as described above.

Besides, in the examples which are shown in FIGS. 3 and 4, the images of light in the fluorescence detection wavelength regions $\lambda a$, $\lambda b$, and $\lambda c$ are written on frame memories a, b, and c for synthesis of fluorescence image that are provided in the control unit that is omitted in the drawings, respectively, in the images into which the light that is selected to be transmitted by the wavelength selection and transmission means 2 is photoelectrically converted by the photo detector means 3. And, the images of light in the spectrum acquisition wavelength regions $\lambda 1, \lambda 2, \ldots, \lambda n$ are written on a frame memory d for acquisition of intensity distribution (refer to FIGS. 3B and 4B).

The fluorescent image compounding means 5 is provided in the control unit that is omitted in the drawings, and combines the images into which light in fluorescence detection wavelength regions that is selected and transmitted by the wavelength selection and transmission means 2 is photoelectrically converted by the photo detector means 3. For example, in the examples which are shown in FIGS. 3 and 4, the fluorescent image compounding means 5 compounds the images of light in the fluorescence detection wavelength ranges $\lambda a$, $\lambda b$, and $\lambda c$ that are written on frame memories a, b, and c for synthesis of fluorescence image.

The image display means 6 displays the image that is synthesized by the fluorescent image compounding means 5. Besides, the image display means 6 may be formed in such a way that the image display means 6 displays not only this image but also the intensity distribution of light in a predetermined wavelength range that is acquired by the below described intensity distribution obtaining means 7.

The intensity distribution obtaining means 7 is provided in the control unit that is omitted in the drawings, and acquires the intensity distribution of light in a predetermined wavelength range by the use of the images into which the light in respective spectrum acquisition wavelength regions in a predetermined wavelength range that is selected to be transmitted by the wavelength selection and transmission means 2 is photoelectrically converted by the photo detector means 3. For example, in the examples which are shown in FIGS. 3 and 4, the intensity distribution obtaining means 7 acquires the intensity distribution of light in a predetermined wavelength range, by the use of the images of light in the spectrum acquisition wavelength regions $\lambda 1, \lambda 2, \ldots, \lambda n$ that are written on the frame memory d for acquisition of intensity distribution.

The wavelength selection control adjusting means 8 is provided in the control unit that is omitted in the drawings. For example, as shown in FIG. 2C, the wavelength selection control adjusting means 8 adjusts the selection and transmission control to the wavelength selection and transmission means 2 by means of the wavelength selection control means 4, in such a way that a fluorescence detection wavelength region corresponding to at least one kind of fluorescence that is selected and transmitted by the wavelength selection and transmission means 2 (the three kinds of the fluorescence detection wavelength regions λa, λb, and λc, in FIG. 2C) is shifted to a peak wavelength region in the intensity distribution of light in the predetermined wavelength range that includes the fluorescence detection wavelength region (the wavelength regions λa', λb', and λc', in FIG. 2C), the intensity distribution being acquired by the intensity distribution obtaining means 7.

In the fluorescent endoscope apparatus of FIG. 1 constituted like this, the excitation light irradiation means 1 irradiates excitation light to an observation area of the living body 9. Fluorescence emitting from the plural kinds of the fluorescent agents that exist in the observation area of the living body 9 and light reflected by the observation area pass through the objective optical system and the image forming optical system that constitute the image pick up optical system in the top end portion of the endoscope that is not shown in the drawings, and light in an excitation wavelength region is blocked by the excitation light cut filter, and the other light enters the wavelength selection and transmission means 2. The wavelength selection and transmission means 2 selects: light in fluorescence detection wavelength regions λa, λb, and λc which correspond to plural kinds of fluorescence that emit from plural kinds of fluorescent agents, respectively, as shown in FIG. 2A for example; and light in spectrum acquisition wavelength regions λ1, λ2, . . . , λn which adjoin each other in turn with a predetermined wavelength width in a predetermined wavelength range that includes the fluorescence detection wavelength regions λa, λb, and λc corresponding to the plural kinds of the fluorescence, as shown in FIG. 2B for example, among the light entering the wavelength selection and transmission means 2, to transmit the selected light, through control by the wavelength selection control means 4, with such timing as is shown in FIG. 3A or 4A for example. The photo detector means 3 photoelectrically converts the light which is selected to be transmitted by the wavelength selection and transmission means 2, and the photoelectrically converted images are written on the frame memories a, b, c, and d which are provided in the control unit that is omitted in the drawings, with such timing as is shown in FIG. 3B or 4B for example. Next, the fluorescent image compounding means 5 combines the images of the light in the fluorescence detection wavelength regions λa, λb, and λc which are written on the frame memories a, b, and c for synthesis of fluorescence image. Also, the intensity distribution obtaining means 7 acquires the intensity distribution of light in a predetermined wavelength range, by the use of the images of the light in the spectrum acquisition wavelength regions λ1, λ2, . . . , λn that are written on the frame memory d for acquisition of intensity distribution. The image display means 6 displays the image which is synthesized by the fluorescent image compounding means 5. Accordingly, in the examples which are shown in FIGS. 3 and 4, the fluorescence image into which the images of the light in the fluorescence detection wavelength regions λa, λb, and λc are combined is displayed as a moving image through the image display means 6, and the intensity distribution of the light in the predetermined wavelength range is acquired through the intensity distribution obtaining means 7 at the background.

In this case, in the fluorescent endoscope apparatus which is shown in FIG. 1, the wavelength selection control adjusting means 8 adjusts control of the wavelength selection and transmission means 2 selecting fluorescence detection wavelength region and transmitting light in the selected fluorescence detection wavelength region through the wavelength selection control means 4, in such a way that a fluorescence detection wavelength region corresponding to at least one kind of fluorescence that is selected to be transmitted by the wavelength selection and transmission means 2 (the three kinds of the fluorescence detection wavelength regions λa, λb, and λc, in FIG. 2C) is shifted to a peak wavelength region in the intensity distribution of light in the predetermined wavelength range that includes the fluorescence detection wavelength region (the wavelength regions λa', λb', and λc', in FIG. 2C), the intensity distribution being acquired by the intensity distribution obtaining means 7, as shown in FIG. 2C.

As a result, according to the fluorescent endoscope apparatus which is shown in FIG. 1, it is possible to display an image in a wavelength range in which light emits with the highest intensity, as a fluorescence image which is displayed as a moving image, so that it is possible to change a wavelength region into a suitable wavelength region for detecting fluorescence in real time to observe the fluorescence image in the living body 9 even though residues or the like cause variation in fluorescence spectrum in the living body 9.

That is to say, according to a fluorescent endoscope apparatus of the present invention, it is possible to acquire fluorescence spectrum for detecting variation in fluorescence spectrum due to residue, difference among individuals, or the like.

Also, according to the fluorescent endoscope apparatus of the present invention, it is possible to select and adjust to a suitable wavelength region for detecting fluorescence which emits from a lesion and a residue in observation of a biological tissue, regardless of the presence or absence of factors in variation in fluorescence spectrum, such as residue and difference among individuals.

Besides, the fluorescent endoscope apparatus which is shown in FIG. 1 may be formed in such a way that: the wavelength selection control means 4 has the first control mode in which the wavelength selection control means 4 controls the wavelength selection and transmission means 2 in such a way that the wavelength selection and transmission means 2 selects light in all of the fluorescence detection wavelength regions (for example, a set of the fluorescence detection wavelength regions λ, λb, and λc in FIG. 4A) to transmit the light in all of the fluorescence detection wavelength regions, and the second control mode in which the wavelength selection control means 4 controls the wavelength selection and transmission means 2 in such a way that the wavelength selection and transmission means 2 selects light in all of the spectrum acquisition wavelength regions (for example, a set of the spectrum acquisition wavelength regions λ1, λ2, . . . , λn in FIG. 4A) to transmit the light in all of the spectrum acquisition wavelength regions; and the wavelength selection control means 4 can be driven through a selection of one of the first and second control modes by a manual operation.

Or, the fluorescent endoscope apparatus which is shown in FIG. 1 may be formed in such a way that: the wavelength selection control means 4 has the first control mode in which the wavelength selection control means 4 controls the wavelength selection and transmission means 2 in such a way that the wavelength selection and transmission means 2 selects light in all of the fluorescence detection wavelength regions (for example, a set of the fluorescence detection wavelength regions λa, λb, and λc in FIG. 3A) to transmit the light in all of the fluorescence detection wavelength regions, and the third control mode in which the wavelength selection control means 4 controls the wavelength selection and transmission means 2 in such a way that, after the wavelength selection and transmission means 2 selects light in all of the fluorescence detection wavelength regions (for example, a set of the fluorescence detection wavelength regions λa, λb, and λc in FIG. 3A) to transmit the light in all of the fluorescence detection wavelength regions, the wavelength selection and transmission means 2 selects light in one spectrum acquisition wavelength region (for example, one of a set of the spectrum acquisition wavelength regions λ1, λ2, . . . , λn in FIG. 3A) to transmit the light in the one spectrum acquisition wavelength region, and a sequence of these processes is repeated until light in all of the spectrum acquisition wavelength region (for example, a set of the spectrum acquisition wavelength regions λ1, λ2, . . . , λn in FIG. 3A) is selected to be transmitted; and the wavelength selection control means 4 can be driven through a selection of one of the first and third control modes by a manual operation.

If the fluorescent endoscope apparatus is formed in such a way that a selection of these control modes can be made by manual operation, an observer can select a control mode so as to acquire a fluorescence spectrum when the moving amount of the top end portion of the endoscope in a living body is small, for example, so that it is possible to minimize position differences between respective spectral images for acquiring the fluorescence spectrum and to acquire the fluorescence spectrum with high precision. Also, in the case where the fluorescent endoscope apparatus is formed in such a way that, at all times, light in a part of the spectrum acquisition wavelength regions is selected to be transmitted on the way to selecting light in all of the fluorescence detection wavelength regions to transmit the light in all of the fluorescence detection wavelength regions by the wavelength selection and transmission means 2, drop frame occurs in a fluorescence image which is displayed by the image display means 6 in selecting spectrum acquisition wavelength region to transmit light in the selected spectrum acquisition wavelength region through the wavelength selection and transmission means 2, when the moving amount of the top end portion of the endoscope in a living body is large. As a result, the image observation becomes troublesome. However, when the fluorescent endoscope apparatus is formed in such a way that a selection of control mode can be made by manual operation, as described above, the observer is also released from the troublesome observation of such a fluorescence image in which drop frame occurs.

Also, in a fluorescent endoscope apparatus which is shown in FIG. 1, it is preferred that the fluorescent endoscope apparatus further comprises a pixel area specifying means which specifies a desired pixel area on which the intensity distribution of light in a predetermined wavelength range is acquired by the intensity distribution obtaining means 7 (where, the pixel area specifying means is omitted in the drawings), and the light intensity distribution obtaining means 7 acquires the intensity distribution of light in the predetermined wavelength range relative to a pixel area which is specified by the pixel area specifying means.

As a result, a detailed spectral analysis only for region on which an analysis of wavelength components is desired is sufficient for a fluorescence image of the living body 9 which is displayed as a moving image, so that it is possible to shorten processing time.

Also, it is preferred that the fluorescent endoscope apparatus which is shown in FIG. 1 is formed in such a way that the wavelength selection control adjusting means 8 automatically makes an adjustment to control of the wavelength selection and transmission means 2 by the wavelength selection control means 4. As a result, an observer can easily operate the fluorescent endoscope apparatus.

Also, the fluorescent endoscope apparatus which is shown in FIG. 1 may be formed in such a way that the wavelength selection control adjusting means 8 manually makes an adjustment to control of the wavelength selection and transmission means 2 by the wavelength selection control means 4. As a result, an observer can adjust a detection wavelength with desired timing at any time.

Also, in a fluorescent endoscope apparatus which is shown in FIG. 1, it is preferred that: the fluorescent endoscope apparatus further comprises a moving amount detecting means which detects a moving amount in an observation area by the use of a change of a fluorescence image which is synthesized by the fluorescence image synthesizing means 5 (where, moving amount detecting means is omitted in the drawings); the wavelength selection control means 4 has the first control mode in which the wavelength selection control means 4 controls the wavelength selection and transmission means 2 in such a way that the wavelength selection and transmission means 2 selects light in all of the fluorescence detection wavelength regions (for example, a set of the fluorescence detection wavelength regions λ, λb, and λc in FIG. 4A) to transmit the light in all of the fluorescence detection wavelength regions, and the second control mode in which the wavelength selection control means 4 controls the wavelength selection and transmission means 2 in such a way that the wavelength selection and transmission means 2 selects light in all of the spectrum acquisition wavelength regions (for example, a set of the spectrum acquisition wavelength regions λ1, λ2, . . . , λn in FIG. 4A) to transmit the light in all of the spectrum acquisition wavelength regions; and, when a moving amount which is detected by the moving amount detecting means is equal to or smaller than a predetermined value, the wavelength selection and transmission means 2 is driven with the second control mode, and when a moving amount which is detected by the moving amount detecting means is larger than the predetermined value, the wavelength selection and transmission means 2 is driven with the first control mode.

Or, in a fluorescent endoscope apparatus which is shown in FIG. 1, it is preferred that: the fluorescent endoscope apparatus further comprises a moving amount detecting means which detects a moving amount in an observation area by the use of a change of a fluorescence image which is synthesized by the fluorescence image synthesizing means 5 (where, moving amount detecting means is omitted in the drawings); the wavelength selection control means 4 has the first control mode in which the wavelength selection control means 4 controls the wavelength selection and transmission means 2 in such a way that the wavelength selection and transmission means 2 selects light in all of the fluorescence detection wavelength regions (for example, a set of the fluorescence detection wavelength regions λa, λb, and λc in FIG. 3A) to transmit the light in all of the fluorescence detection wavelength regions, and the third control mode in which the wavelength selection control means 4 controls the wavelength selection and transmission means 2 in such a way that, after the wavelength selection and transmission means 2 selects light in all of the fluorescence detection wavelength regions (for example, a set of the fluorescence detection wavelength regions λa, λb, and λc in FIG. 3A) to transmit the light in all of the fluorescence detection wavelength regions, the wavelength selection and transmission means 2 selects light in one spectrum acquisition wavelength region (for example, one of a set of the spectrum acquisition wavelength regions λ1, λ2, . . . , λn in FIG. 3A) to transmit the light in the one spectrum acquisition wavelength region, and a sequence of these processes is repeated until light in all of the spectrum acquisition wavelength region (for example, a set of the spectrum acquisition wavelength regions λ1, λ2, . . . , λn in FIG. 3A) is selected to be transmitted; and, when a moving amount which is detected by the moving amount detecting means is equal to or smaller than a predetermined value, the wavelength selection and transmission means 2 is driven with the third control mode, and when a moving amount which is detected by the moving amount detecting means is larger than the predetermined value, the wavelength selection and transmission means 2 is driven with the first control mode.

As in these fluorescent endoscope apparatuses, when a fluorescent endoscope apparatus of the present invention is formed in such a way that a moving amount in an observation area is detected by the use of a change of a fluorescence image through the moving amount detecting means (which is omitted in the drawings) and light in spectrum acquisition wavelength region is selected to transmitted when the moving amount is equal to or smaller than a predetermined value, such a formation of the fluorescent endoscope apparatus saves an observer from making a selection of control mode, and, as described above, the observer is also released from the troublesomeness of drop frame in fluorescence image.

Also, in this case, it is preferred that the intensity distribution obtaining means 7 operates when a moving amount which is detected by the moving amount detecting means (which is omitted in the drawings) is equal to or smaller than the predetermined value. As a result, the precision in an acquired fluorescence spectrum becomes high.

Also, in a fluorescent endoscope apparatus which is shown in FIG. 1, it is preferred that the fluorescent endoscope apparatus further comprises a moving amount detecting means which detects a moving amount in an observation area by the use of a change of a fluorescence image which is synthesized by the fluorescence image synthesizing means 5 (where, the moving amount detecting means is omitted in the drawings), and the intensity distribution obtaining means 7 operates when a moving amount which is detected by the moving amount detecting means is equal to or smaller than a predetermined value. As a result, the precision in an acquired fluorescence spectrum becomes high.

Also, in a fluorescent endoscope apparatus which is shown in FIG. 1, it is preferred that, even though the wavelength selection control means 4 is formed in such a way that the wavelength selection control means 4 does not have control modes as described above, the intensity distribution obtaining means 7 further includes a targeted wavelength region setting means which can set a predetermined wavelength range that becomes a target range for acquisition of intensity distribution, (where, the targeted wavelength range setting means is omitted in the drawings). As a result, it is possible to observe a desired fluorescence image with the optimum detection wavelength in accordance with various observation objects and various purposes of test.

Also, in a fluorescent endoscope apparatus which is shown in FIG. 1, it is preferred that the fluorescent endoscope apparatus further comprises a spectrum division means which divides a specific spectrum by the use of the intensity distribution of light in a predetermined wavelength range which is acquired by the intensity distribution obtaining means 7 (where, the spectrum division means is omitted in the drawings). As a result, the precision in detecting the optimum wavelength region for a desired fluorescence substance becomes high.

Also, in a fluorescent endoscope apparatus which is shown in FIG. 1, it is preferred that the image display means 6 displays the intensity distribution of light in a predetermined wavelength range which is acquired by the intensity distribution obtaining means 7, together with an image which is synthesized by the fluorescent image compounding means 5. As a result, it is possible to observe the information about the fluorescence image in an observation area in the living body 9 and the fluorescence spectrum information together without changing a screen into another one.

Fluorescent endoscope apparatuses according to the embodiments of the present invention will be explained below using the drawings.

Figure 5:
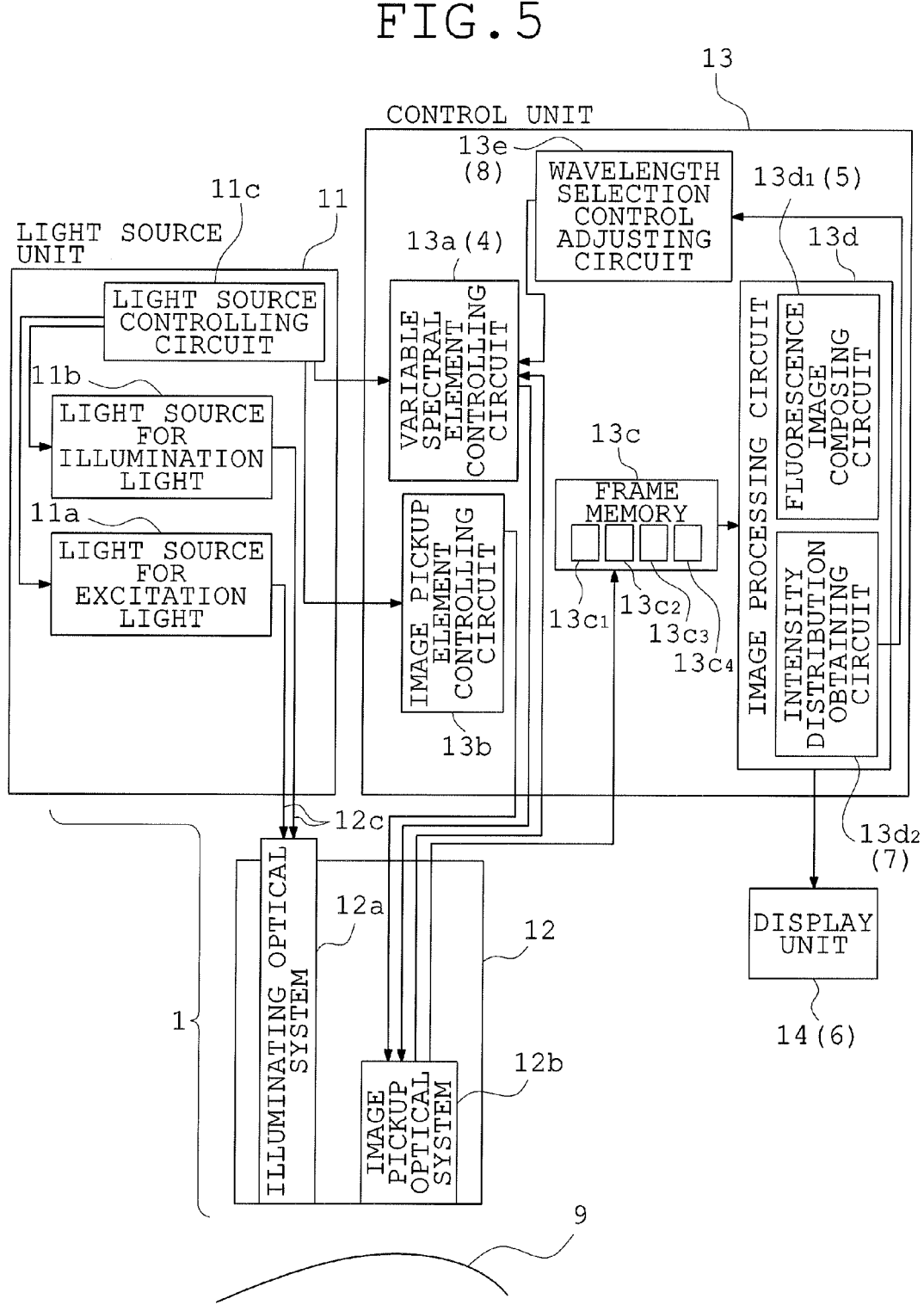
FIG. 5 is a block diagram schematically showing a common constitution to fluorescent endoscope apparatuses of the respective embodiments of the present invention.
Figure 6:
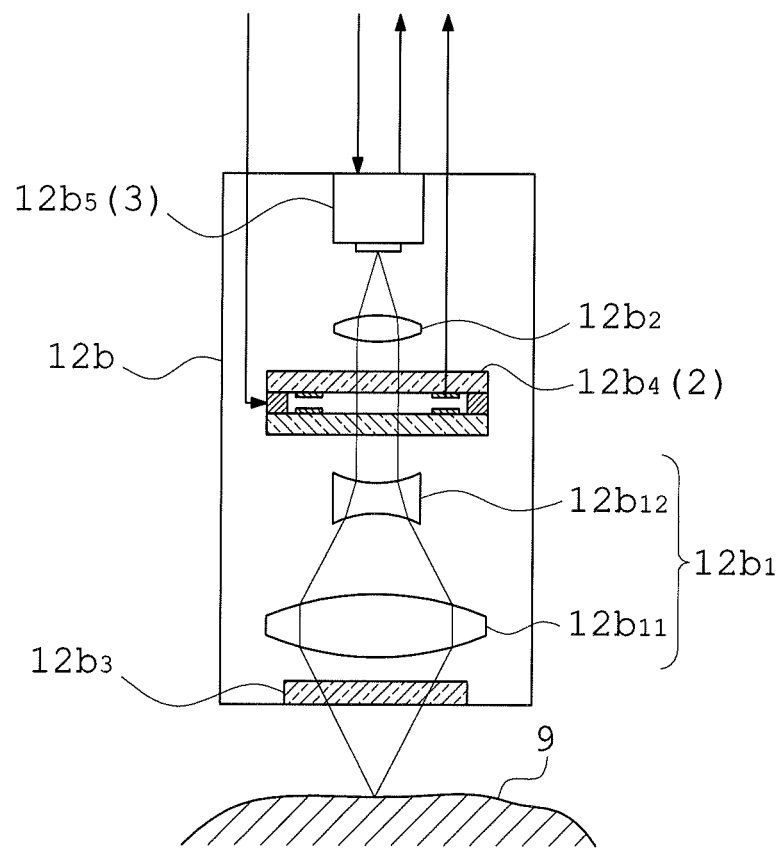
FIG. 6 is an explanatory view showing one example of the constitution of an image pick up optical system for the fluorescent endoscope apparatus shown in FIG. 5.
Figure 7:
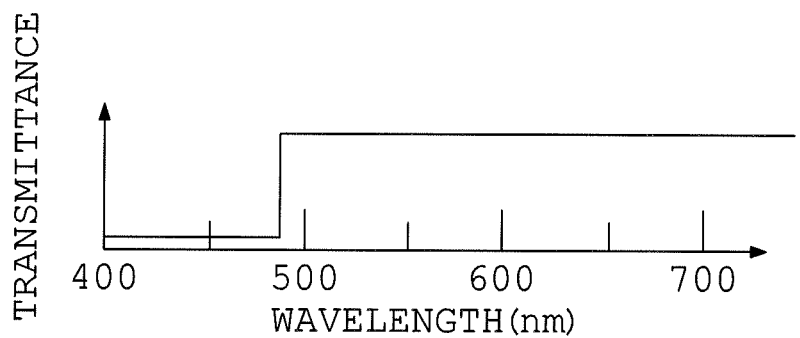
FIG. 7 is a graph showing the transmittable wavelength characteristic of an excitation light cut filter which is used in an image pick up optical system for the fluorescent endoscope apparatus shown in FIG. 5.

FIG. 5 is a block diagram schematically showing a common constitution to fluorescent endoscope apparatuses of the respective embodiments of the present invention. FIG. 6 is an explanatory view showing one example of the constitution of an image pick up optical system for the fluorescent endoscope apparatus shown in FIG. 5. FIG. 7 is a graph showing the transmittable wavelength characteristic of an excitation light cut filter which is used in an image pick up optical system for the fluorescent endoscope apparatus shown in FIG. 5. FIG. 8 is a graph showing the spectral transmittance characteristic of plural kinds of fluorescence which exists in a living body that is an object for observation in the fluorescent endoscope apparatus shown in FIG. 5.

The fluorescent endoscope apparatus which is shown in FIG. 5 includes a light source unit 11, an endoscope top end insertion unit 12, a control unit 13, and a display unit 14.

The light source unit 11 includes an light source 11a for excitation light, an light source 11b for illumination light, and a light source controlling circuit 11c.

The excitation light source unit 11a includes a light source (which is omitted in the drawings) and an excitation filter (which is omitted in the drawings), and is formed in such a way that the light source 11a for excitation light emits light in a predetermined wavelength range for excitation.

The light source 11b for illumination light is composed of a light source which emits light in the usual visible wavelength range (and is omitted in the drawings).

The light source controlling circuit 11c is formed in such a way that the light source controlling circuit 11c can perform control of selectively switching excitation light from the light source 11a for excitation light and illumination light from the light source 11b for illumination light as light emitting from the light source unit 11, for example, by rotating a turret which is provided with an excitation filter and a transparent glass plate on circumference, or by sliding a slider which is provided with an excitation filter and a transparent glass plate.

The endoscope top end insertion unit 12 includes an illumination optical system 12a and an image pick up optical system 12b. The illumination optical system 12a irradiates to the living body 9 light from the light source unit 11 through the light guide 12c.

And, the light source 11a for excitation light in the light source unit 11, the light guide 12c, and the illumination optical system 12a are combined with one another and have a function as a excitation light irradiation means 1 which irradiates to an observation area of the living body 9 excitation light that excites plural kinds of fluorescent agents existing in the observation area.

The image pick up optical system 12b includes an objective optical system $12b_1$, an image forming optical system $12b_2$, an excitation light cut filter $12b_3$, a spectral optical element $12b_4$, and an image sensor $12b_5$, as shown in FIG. 6.

It is optical characteristic of the excitation light cut filter $12b_3$ to block light in a wavelength range of 400 to 480 nm of a wavelength range of 400 to 700 nm and to transmit light in the other of the wavelength range of 400 to 700 nm, as shown in FIG. 7 for example.

The spectral optical element $12b_4$ is composed of an etalon or the like, functions as a wavelength selection and transmission means 2, and selects and transmits light in a predetermined wavelength range among light entering from the observation area of the living body 9, through the wavelength selection control means 4 that is described below.

The image sensor $12b_5$ is composed of a black and white CCD that consists of a single chip image sensor for example, functions as a photo detector means 3, and photoelectrically converts light which is selected to be transmitted by the spectral optical element $12b_4$ (the wavelength selection and transmission means 2). An image into which the transmitted light is photoelectrically converted is written on a frame memory 13c that is provided in a control unit 13, the control unit 13 being shown in FIG. 5 and described below.

The control unit 13 includes a variable spectral element controlling circuit 13a, an image pick up element control circuit 13b, the frame memory 13c, an image processing circuit 13d, and a wavelength selection control adjustment circuit 13e.

The variable spectral element controlling circuit 13a functions as a wavelength selection control means 4.

The frame memory 13c includes an R frame memory $13c_1$ for synthesis of fluorescence image, a G frame memory $13c_2$ for synthesis of fluorescence image, a B frame memory $13c_3$ for synthesis of fluorescence image, and a frame memory $13c_4$ for acquisition of intensity distribution.

Images into which light in fluorescence detection wavelength region that is selected to transmitted by the wavelength selection and transmission means 2 is photoelectrically converted by the photo detector means 3 are written on the R frame memory $13c_1$, the G frame memory $13c_2$, and the B frame memory $13c_3$ for synthesis of fluorescence image, respectively.

A image into which light in spectrum acquisition wavelength region that is selected to be transmitted by the wavelength selection and transmission means 2 is photoelectrically converted by the photo detector means 3 is written on the frame memory $13c_4$ for acquisition of intensity distribution.

The image pick up element control circuit 13b performs control of operating the image sensor $12b_5$ (the photo detector means 3).

The image processing circuit 13d includes a fluorescence image composing circuit $13d_1$ and an intensity distribution obtaining circuit $13d_2$.

The fluorescence image composing circuit $13d_1$ functions as a fluorescent image compounding means 5 and combines respective image signals which are written on the R frame memory $13c_1$, the G frame memory $13c_2$, and the B frame memory $13c_3$ for synthesis of fluorescence image. In this case, the image signals are converted into output signals having various color phases, in order to make it easy to distinguish normal tissue region and lesion tissue region.

The display unit 14 functions as an image display means 6 and displays an image which is synthesized by the fluorescence image composing circuit $13d_1$ (the fluorescent image compounding means 5). Besides, the display unit 14 may further display also the intensity distribution of light in a predetermined wavelength range which is acquired by the intensity distribution obtaining circuit $13d_2$ that is described below.

The intensity distribution obtaining circuit $13d_2$ functions as an intensity distribution obtaining means 7 and acquires the intensity distribution of light in a predetermined wavelength range by the use of the images into which light in respective spectrum acquisition wavelength regions in the predetermined wavelength range that is selected to be transmitted by the spectral optical element $12b_4$ (the wavelength selection and transmission means 2) is photoelectrically converted by the image sensor $12b_5$ (the photo detector means 3).

The wavelength selection control adjustment circuit 13e functions as a wavelength selection control adjusting means 8 and adjusts control of the spectral optical element $12b_4$ (the wavelength selection and transmission means 2) selecting fluorescence detection wavelength region and transmitting light in the selected fluorescence detection wavelength region by the variable spectral element controlling circuit 13a (the wavelength selection control means 4), in such a way that a fluorescence detection wavelength region corresponding to at least one kind of fluorescence that is selected to be transmitted by the spectral optical element $12b_4$ (the wavelength selection and transmission means 2) (the three kinds of the fluorescence detection wavelength regions λ, λb, and λc, in FIG. 2C) is shifted to a peak wavelength region in the intensity distribution of light in a predetermined wavelength range that includes the fluorescence detection wavelength region (the wavelength regions λa', λb', and λc', in FIG. 2C), the intensity distribution being acquired by the intensity distribution obtaining circuit $13d_2$ (the intensity distribution obtaining means 7), as shown in FIG. 2C for example.

Besides, as shown in FIG. 8, the biological tissue 9 which is an object for observation in the respective following embodiments is labeled with a fluorescent agent as a fluorescent probe which emits fluorescence in a wavelength range of 500 to 600 nm by radiating to the fluorescent agent excitation light the wavelength of which is less than 475 nm. Also, the biological tissue 9 emits auto-fluorescence which is in a wavelength range of 475 to 750 nm and the peak wavelength region of which is a predetermined wavelength region in a wavelength range of 500 to 550 nm, by radiating this excitation light to the biological tissue 9. Also, feces which are a residue in the biological tissue 9 also emits auto-fluorescence which is in a wavelength range of 475 to 750 nm and the peak wavelength region of which is a predetermined wavelength region in a wavelength range of 650 to 700 nm. Besides, the shapes of the fluorescence spectra of these fluorescences vary with difference among individual subjects or subject's condition (the amount of residue, the presence or absence of hemorrhage, or the like).

Besides, for example, the image sensor $12b_5$ may be composed of a color CCD which is provided with a mosaic filter (which is omitted in the drawings) and a single chip image sensor (which is omitted in the drawings).

In this case, for example, the mosaic filter should be formed in such a way that a large number of filters that transmit light in a wavelength range of R (575 to 695 nm) (and is omitted in the drawings), a large number of filters that transmit light in a wavelength range of G (460 to 600 nm) (and is omitted in the drawings), and a large number of filters that transmit light in a wavelength range of B (380 to 490 nm) (and is omitted in the drawings) are arranged in a mosaic manner.

Also, the single chip image sensor should be formed in such a way that: the pixels of the single chip image sensor correspond to the filters that transmit light in a wavelength range of R (575 to 695 nm), the filters that transmit light in a wavelength range of G (460 to 600 nm), and the filters that transmit light in a wavelength range of B (380 to 490 nm), respectively, these filters constituting the mosaic filter; and plural kinds of light into which the light of the image is divided by the mosaic filter are acquired by the different pixels, separately.

Also, in this case, the fluorescent endoscope apparatus should be formed in such a way that the R frame memory $13c_1$, the G frame memory $13c_2$, and the B frame memory $13c_3$ for synthesis of fluorescence image correspond to the filters that transmit light in a wavelength range of R (575 to 695 nm), the filters that transmit light in a wavelength range of G (460 to 600 nm), and the filters that transmit light in a wavelength range of B (380 to 490 nm), respectively, these filters constituting the mosaic filter, and the image signals which are separated from one another through the mosaic filter and are acquired by the corresponding pixels respectively are written on these frame memories separately.

FIG. 9 is an explanatory view showing the relation between an image and a spectrum which are acquired with the fluorescent endoscope apparatus shown in FIG. 5, FIG. 9A is a view showing the images of light in three kinds of fluorescence detection wavelength regions, which are written on respective frame memories $13c_1$, $13c_2$, and $13c_3$ for synthesis of fluorescence image, and showing an image into which these images are combined by the fluorescent image compounding means 5 and which is displayed by the image display means 6, and FIG. 9B is a graph showing the images of light in spectrum acquisition wavelength regions extending throughout a predetermined wavelength range, which are recorded on a frame memory $13c_4$ for acquisition of intensity distribution, and showing a fluorescence spectrum at a predetermined image position, which is acquired by the intensity distribution obtaining means 7 by the use of these images. Besides, the fluorescent endoscope apparatus which is shown in FIG. 5 is provided with the above described pixel area specifying means (which is omitted in the drawings), and, in FIG. 9, for the sake of convenience, FIG. 9A is made to show a state where a region in which a fluorescent agent with which the biological tissue is labeled emits light strongly (pixel area) and a region in which a feces that is a residue in the biological tissue emits fluorescence strongly (pixel area) are specified in the fluorescence image of the living body 9 that is displayed by the image display means 6, and FIG. 9B is made to show the fluorescence spectrum of the fluorescent agent with which the biological tissue is labeled and the fluorescence spectrum of the feces which is a residue in the biological tissue, in the pixel areas which are specified in FIG. 9A respectively.

Also, the fluorescent endoscope apparatuses of the respective embodiments are provided with the spectrum division means (which is not shown in the drawings and) as described in the fluorescent endoscope apparatus which is shown in FIG. 1.

The spectrum division means is a control circuit which is provided in the control unit 13. And, the spectrum division means is formed in such a way that the spectrum division means can divide a multiplexed fluorescence image into separate fluorescences by calculating the densities of respective fluorescent dyes from the multiplexed fluorescence image, for example with methods such as spectral estimation and Unmixing. The use of the spectrum division means improves a precision in detecting a suitable wavelength region for a desired fluorescent substance.

Now, a method for the division into fluorescences through Unmixing is conceptually explained using FIG. 10.

FIG. 10 is an explanatory view conceptually showing a method for dividing a fluorescence spectrum by which is acquired by the intensity distribution obtaining means 7 and in which plural kinds of fluorescence components intermingle with one another, into its respective fluorescence components, FIG. 10A is a graph showing the spectra of auto-fluorescence originating from a living body and of fluorescence emitting from a fluorescent agent for labeling the living body, which is already known to be contained in the living body in advance, respectively, FIG. 10B is a graph showing one example of a fluorescence spectrum which is acquired by the intensity distribution obtaining means 7, and FIG. 10C is a graph showing the fluorescence spectrum which is shown in FIG. 10B and is divided into its fluorescence components by the spectrum division means. Besides, in this case, two kinds of fluorescent dyes (auto-fluorescence originating from the living body and fluorescent agent) are considered to have already known to be present in the biological tissue 9.

First, the fluorescence spectrum of each of the fluorescent dyes which exist in a tissue of the living body 9 that is an object for measurement is measured at a predetermined standard density, in advance. In this case, FIG. 10A shows one example of each of fluorescence spectra of the two kinds of the fluorescent dyes at the standard density.

Next, the fluorescence spectrum of the tissue of the living body 9 in which the two kind of the fluorescent dyes are already known to exist is measured. FIG. 10B shows one example of the fluorescence spectrum of the tissue of the living body 9 which is acquired by the intensity distribution obtaining means 7.

Next, the densities of the two kinds of the fluorescent dyes for obtaining the measurement data of the fluorescence spectrum of the tissue of the living body 9 which is shown in FIG. 10B are calculated by the use of the measurement data of the fluorescence spectra of the respective two kinds of the fluorescent dyes at the standard density, the fluorescence spectra being shown in FIG. 10A, and the fluorescence spectrum shown in FIG. 10B is divided into the fluorescence spectra of the respective fluorescent dyes by the use of the calculation results. FIG. 10C schematically shows an example of the division of the measurement data of the fluorescence spectrum of the tissue of the living body 9 shown in FIG. 10B into the fluorescence spectra of the respective two kinds of the fluorescent dyes at a predetermined density.

Next, a method to calculate the density of each of the fluorescent dyes in Unmixing is explained.

The signal intensity $I_{all}(\lambda n)$ of an object to be measured at a wavelength $\lambda n$ is the sum of the signal intensities of the respective fluorescent dyes at the wavelength $\lambda n$ and is expressed by the following equation (1):

$$I_{all}(\lambda n) = I1(\lambda n) + I2(\lambda n) + \ldots + Im(\lambda n) \quad (1)$$

where I1 denotes the signal intensity at the wavelength $\lambda n$ which is obtained from a fluorescent dye 1, I2 denotes the signal intensity at a wavelength $\lambda n$ which is obtained from a fluorescent dye 2, and Im denotes the signal intensity at a wavelength $\lambda n$ which is obtained from a fluorescent dye m.

Now, the signal intensity which is obtained from each of the fluorescent dyes is proportional to the density of each of the fluorescent dyes. Accordingly, in the case where m kinds of fluorescent dyes exist in the object to be measured, the signal intensities at a wavelength $\lambda n$ which are obtained from the respective fluorescent dyes can be expressed by the following equations (2a) to (2c):

$$I1(\lambda n) = a1(\lambda n) * D1 \quad (2a)$$

where D1 denotes the density of the fluorescent dye 1, and a1 $(\lambda n)$ denotes the coefficient for the fluorescent dye 1 at the standard density at the wavelength $\lambda n$.

$$I2(\lambda n) = a2(\lambda n) * D2 \quad (2b)$$

where D2 denotes the density of the fluorescent dye 2, and a2 $(\lambda n)$ denotes the coefficient for the fluorescent dye 2 at the standard density at the wavelength $\lambda n$.

$$Im(\lambda n) = am(\lambda n) * Dm \quad (2c)$$

where Dm denotes the density of the fluorescent dye m, and am $(\lambda n)$ denotes the coefficient for the fluorescent dye m at the standard density at the wavelength $\lambda n$.

In the case where it is supposed that m kinds of the fluorescent dyes exist in the object to be measured, the signal intensities of the measured object at n kinds of wavelengths λ1 to λn can be expressed, for example, by the following matrix equation (3) with these equations (2a) to (2c):

$$\begin{pmatrix} I_{all}(\lambda 1) \\ I_{all}(\lambda 2) \\ \vdots \\ I_{all}(\lambda n) \end{pmatrix} = \begin{pmatrix} a1(\lambda 1) & a2(\lambda 1) & \ldots & am(\lambda 1) \\ a1(\lambda 2) & a2(\lambda 2) & \ldots & am(\lambda 2) \\ \vdots & \vdots & \vdots & \vdots \\ a1(\lambda n) & a2(\lambda n) & \ldots & am(\lambda n) \end{pmatrix} \begin{pmatrix} D1 \\ D2 \\ \vdots \\ Dn \end{pmatrix} \quad (3)$$

In this case, in the left side of the matrix equation (3), $$\begin{pmatrix} I_{all}(\lambda 1) \\ I_{all}(\lambda 2) \\ \vdots \\ I_{all}(\lambda n) \end{pmatrix}$$

denotes the spectrum of the object to be measured.

Also, in the right side of the matrix equation (3), $$\begin{pmatrix} a1(\lambda 1) & a2(\lambda 1) & \ldots & am(\lambda 1) \\ a1(\lambda 2) & a2(\lambda 2) & \ldots & am(\lambda 2) \\ \vdots & \vdots & \vdots & \vdots \\ a1(\lambda n) & a2(\lambda n) & \ldots & am(\lambda n) \end{pmatrix}$$

denotes the fluorescent spectra of the respective fluorescent dyes at the standard density.

Accordingly, the densities D1, D2, . . . , and Dm of the respective fluorescent dyes are found by solving the following matrix equation (4):

$$\begin{pmatrix} D1 \\ D2 \\ \vdots \\ Dn \end{pmatrix} = \begin{pmatrix} a1(\lambda 1) & a2(\lambda 1) & \ldots & am(\lambda 1) \\ a1(\lambda 2) & a2(\lambda 2) & \ldots & am(\lambda 2) \\ \vdots & \vdots & \vdots & \vdots \\ a1(\lambda n) & a2(\lambda n) & \ldots & am(\lambda n) \end{pmatrix}^{-1} \begin{pmatrix} I_{all}(\lambda 1) \\ I_{all}(\lambda 2) \\ \vdots \\ I_{all}(\lambda n) \end{pmatrix} \quad (4)$$

Besides, in the above described matrix equation, when the number of varieties of the spectral images is equal to that of varieties of the fluorescent dyes (or, n=m), the equations are as many as varieties of the densities of the fluorescent dyes, so that the matrix equation can be uniquely solved. Also, when the number of varieties of the spectral images is larger than that of varieties of the fluorescent dyes (or, n>m), although the number of the equations is larger than that of varieties of the densities of the fluorescent dyes, the matrix equation can be solved with the least squares method, in this case. As compared with this, when the number of varieties of the spectral images is smaller than that of varieties of the fluorescent dyes (or, n<m), the number of the equations is smaller than that of varieties of the densities of the fluorescent dyes, so that the matrix equation cannot be solved.

Accordingly, the method of Unmixing requires the premise that the number of varieties of the spectral images is equal to or larger than that of varieties of the fluorescent dyes (or, n≥m), In such a manner, the fluorescence spectra of known fluorescence components are separated from one another by the spectrum division means. Also, in this case, when the fluorescence spectra of the known fluorescence components are separated from the fluorescence spectrum which is acquired by the intensity distribution obtaining means 7 and in which plural kinds of fluorescence components intermingle with one another, it is also possible to estimate the fluorescence spectrum of an unknown fluorescence component (which is the fluorescence component from residue in this case).

Besides, the fluorescence spectrum characteristic (or characteristic points) of known fluorescence components may be registered in a memory in the endoscope top end insertion unit 12 or the control unit 13 (where, the memory is omitted in the drawings), in advance.

Wavelength regions which form an extreme value in the spectra of the respective fluorescence components that are separated from one another by the spectrum division means are extracted as a peak wavelength region in the intensity distribution of light in the predetermined wavelength range including the fluorescence detection wavelength region which is acquired by the intensity distribution obtaining circuit $13d_2$ (the intensity distribution obtaining means 7), by the wavelength selection control adjustment circuit $13e$ (the wavelength selection control adjusting means 8). And, the wavelength selection control adjustment circuit $13e$ adjusts control of the spectral optical element $12b_4$ (the wavelength selection and transmission means 2) selecting fluorescence detection wavelength region and transmitting light in the selected fluorescence detection wavelength region through the variable spectral element controlling circuit $13a$ (the wavelength selection control means 4), in such a way that when a fluorescence detection wavelength region corresponding to at least one kind of fluorescence that is selected to be transmitted by the spectral optical element $12b_4$ (the wavelength selection and transmission means 2) (the three kinds of the fluorescence detection wavelength regions λ, λb, and λc, in FIG. 2C) does not corresponds with the extracted peak wavelength region, the fluorescence detection wavelength region is shifted to the peak wavelength region (the wavelength regions λa', λb', and λc', in FIG. 2C).

The other fundamental constitutions and operation effects are approximately the same as those of the fluorescent endoscope apparatus which was explained using FIG. 1.

Embodiment 1

Figure 11A:
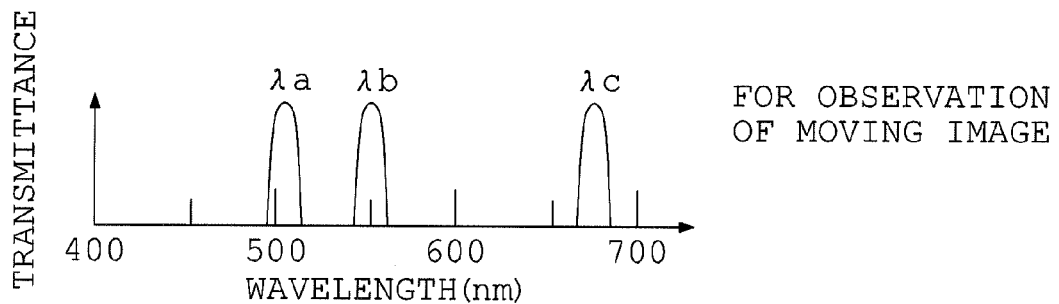
FIG. 11A is a view showing respective fluorescence detection wavelength regions.
Figure 11B:
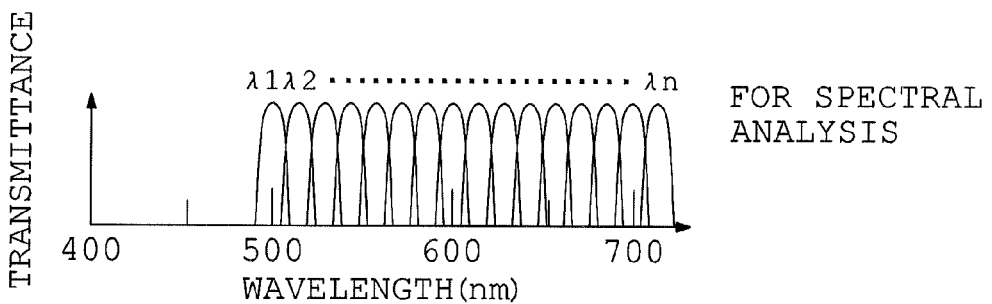
FIG. 11B is a view showing respective spectrum acquisition wavelength regions.
Figure 11C:
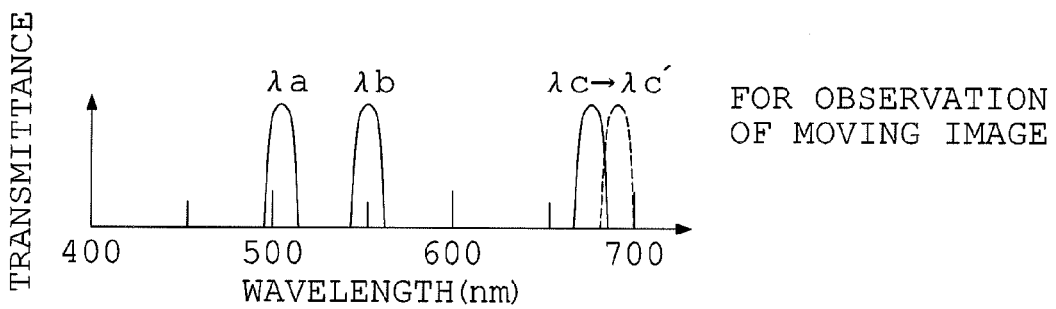
FIG. 11C is a view showing a state in which one fluorescence detection wavelength region is shifted.
Figure 12A:
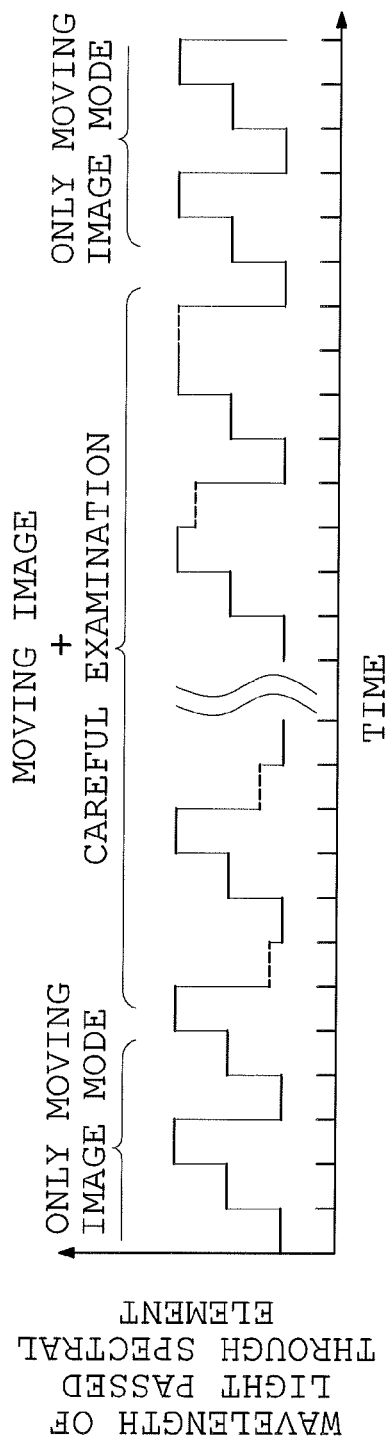
FIG. 12A is a view chronologically showing light in respective wavelength regions which the wavelength selection and transmission means selects and transmits the light in the wavelength regions.
Figure 12B:
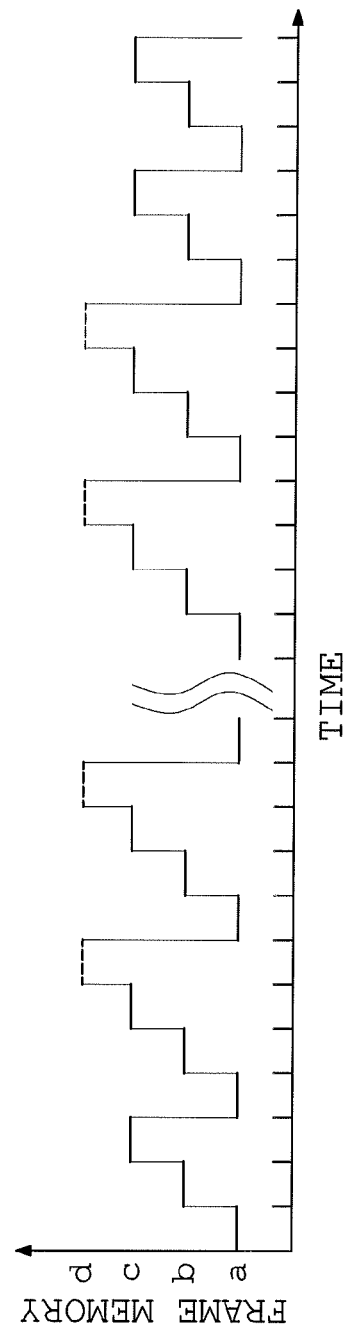
FIG. 12B is a view chronologically showing light in respective wavelength regions which is photoelectrically converted at approximately the same time as FIG. 12A through the photo detector means, to be recorded on respective frame memories.
Figures 13A, 13B:
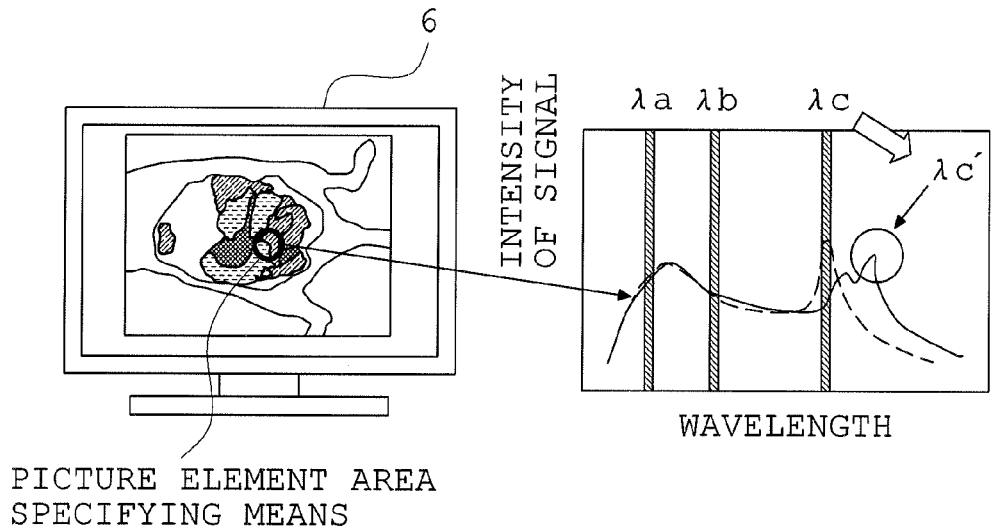
FIG. 13A is a view showing an image into which the images of light in three kinds of fluorescence detection wavelength regions that are written on respective frame memories for synthesis of fluorescence image are combined by the fluorescent image compounding means and which is displayed by the image display means.
FIG. 13B is a graph showing a state in which a peak wavelength region of the fluorescence spectrum of a residue that is acquired by the intensity distribution obtaining means relative to a pixel area specified through the pixel area specifying means is shifted from the peak wavelength region of a known fluorescence spectrum in the fluorescence image shown in FIG. 13A.

FIG. 11 is a view showing one example of wavelength region which the wavelength selection and transmission means 2 selects to transmit light in the wavelength region in fluorescent endoscope apparatus according to the embodiment 1, FIG. 11A is a view showing respective fluorescence detection wavelength regions, FIG. 11B is a view showing respective spectrum acquisition wavelength regions, FIG. 11C is a view showing a state in which one fluorescence detection wavelength region is shifted. FIG. 12 is an explanatory view showing one variation of timing to acquire a spectral image in the fluorescent endoscope apparatus of the embodiment 1, FIG. 12A is a view chronologically showing light in respective wavelength regions which the wavelength selection and transmission means 2 selects to transmit the light in the wavelength regions, and FIG. 12B is a view chronologically showing light in respective wavelength regions which is photoelectrically converted at approximately the same time as FIG. 12A through the photo detector means, to be recorded on respective frame memories $13c_1$, $13c_2$, $13c_3$, and $13c_4$. FIG. 13 is an explanatory view showing a fluorescence image which is displayed by the image display means 6 and showing a fluorescence spectrum which is acquired by the intensity distribution obtaining means 7 in the fluorescent endoscope apparatus of the embodiment 1, FIG. 13A is a view showing an image into which the images of light in three kinds of fluorescence detection wavelength regions that are written on respective frame memories $13c_1$, $13c_2$, and $13c_3$ for synthesis of fluorescence image are combined by the fluorescent image compounding means 5 and which is displayed by the image display means 6, and FIG. 13B is a graph showing a state in which a peak wavelength region of the fluorescence spectrum of a residue that is acquired by the intensity distribution obtaining means 7 relative to a pixel area specified through the pixel area specifying means is shifted from the peak wavelength region of a known fluorescence spectrum in the fluorescence image shown in FIG. 13A.

The fluorescent endoscope apparatus of the embodiment 1 has the same fundamental constitution as explained above using FIGS. 5 to 10. In the fluorescent endoscope apparatus of the embodiment 1, the wavelength selection control means 4 controls the wavelength selection and transmission means 2 in such a way that the wavelength selection and transmission means 2 selects: light in fluorescence detection wavelength regions $\lambda a$, $\lambda b$, and $\lambda c$ which correspond to three kinds of fluorescence (auto-fluorescence, fluorescence emitting from fluorescent agent, and fluorescence emitting from feces that is a residue) that emit from three kinds of fluorescent agents that are shown in FIG. 8, respectively, as shown in FIG. 11; and light in spectrum acquisition wavelength regions $\lambda 1$, $\lambda 2$, ..., $\lambda n$ which adjoin each other in turn with a predetermined wavelength width in a wavelength range of 490 to 730 nm that includes the fluorescence detection wavelength regions $\lambda$, $\lambda b$, and $\lambda c$, to transmit the selected light.

In addition, the wavelength selection control means 4 controls the wavelength selection and transmission means 2 in such a way that: timing with which the wavelength selection and transmission means 2 selects fluorescence detection wavelength region and spectrum acquisition wavelength region to transmit light in the wavelength regions is such that the wavelength selection and transmission means 2 selects light in one spectrum acquisition wavelength region to transmit the light in the one spectrum acquisition wavelength region after selecting light in all of the fluorescence detection wavelength regions $\lambda a$, $\lambda b$, and $\lambda c$ to transmit the light in all of the fluorescence detection wavelength regions, as shown in FIG. 3A; and a sequence of these processes is repeated until light in all of the spectrum acquisition wavelength regions is selected to be transmitted. That is to say, after fluorescence images are acquired as a moving image with the three RGB frames $13c_1$, $13c_2$, and $13c_3$, one spectral image is acquired with the frame $13c_4$ for acquiring fluorescence spectrum.

And, the fluorescent endoscope apparatus of the embodiment 1 acquires the fluorescence spectrum at the background while acquiring the moving image of the fluorescence image to display the moving image, by such control by the wavelength selection control means 4.

Besides, the wavelength selection control means 4 may control the wavelength selection and transmission means 2 in such a way that timing with which the wavelength selection and transmission means 2 selects fluorescence detection wavelength region and spectrum acquisition wavelength region to transmit light in the wavelength regions is such that the wavelength selection and transmission means 2 selects light in all of the spectrum acquisition wavelength regions $\lambda 1$, $\lambda 2$, ..., $\lambda n$ to transmit the light in all of the spectrum acquisition wavelength regions after selecting light in all of the fluorescence detection wavelength regions $\lambda a$, $\lambda b$, and $\lambda c$ to transmit the light in all of the fluorescence detection wavelength regions, as shown in FIG. 4A. For example, when the endoscope top end insertion unit 12 is made to become motionless in the living body, fluorescence spectra may be automatically or manually acquired all together, through the above described moving amount detecting means (which is omitted in the drawings).

In this case, fluorescence images for moving image are written on the frame memories $13c_1$, $13c_2$, and $13c_3$ for synthesis of fluorescence image. And, the image display means 6 displays the written fluorescence images frame by frame or as a still image, while the spectral images are being acquired.

In addition, as shown in FIG. 12, the spectral image may be acquired with desired timing on which an observer focuses. That is to say, for example, the fluorescent endoscope apparatus of the embodiment 1 may be formed in such a way that: the wavelength selection control means 4 has the first control mode in which the wavelength selection control means 4 controls the wavelength selection and transmission means 2 in such a way that the wavelength selection and transmission means 2 selects light in all of the fluorescence detection wavelength regions (for example, a set of the fluorescence detection wavelength regions $\lambda a$, $\lambda b$, and $\lambda c$ in FIG. 3A) to transmit the light in all of the fluorescence detection wavelength regions, and the third control mode in which the wavelength selection control means 4 controls the wavelength selection and transmission means 2 in such a way that, after the wavelength selection and transmission means 2 selects light in all of the fluorescence detection wavelength regions (for example, a set of the fluorescence detection wavelength regions $\lambda a$, $\lambda b$, and $\lambda c$ in FIG. 3A) to transmit the light in all of the fluorescence detection wavelength regions, the wavelength selection and transmission means 2 selects light in one spectrum acquisition wavelength region (for example, one of a set of the spectrum acquisition wavelength regions $\lambda 1$, $\lambda 2$, ..., $\lambda n$ in FIG. 3A) to transmit the light in the one spectrum acquisition wavelength region, and a sequence of these processes is repeated until light in all of the spectrum acquisition wavelength region (for example, a set of the spectrum acquisition wavelength regions $k1$, $\lambda 2$, ..., $\lambda n$ in FIG. 3A) is selected to be transmitted; and the wavelength selection control means can be driven through a selection of one of the first and third control modes by a manual operation.

Also, the fluorescent endoscope apparatus of the embodiment 1 may be formed in such a way that one of the above described mode in which only a moving image of fluorescence image is displayed and the mode in which a spectral image is acquired at the back while a moving image of fluorescence image is being displayed is automatically changed into the other to drive the wavelength selection control means 4.

Also, as shown in FIG. 13A, the fluorescent endoscope apparatus of the embodiment 1 is formed in such a way that the observer can manually input and specify an area on which the observer desires to display the spectrum in a screen on which a fluorescence image is displayed by the displaying unit 6, through the pixel area specifying means. In order to input and specify an area in the screen on which the observer desires to display the spectrum, for example, a pointer on the screen, a border indicating the area, or the like is operated using keyboard or mouse which is not shown in the drawings. Besides, FIG. 13A shows a state in which a pixel area relative to a region of a residue that emits fluorescence strongly is specified. And, the fluorescent endoscope apparatus of the embodiment 1 is formed in such a way that the intensity distribution obtaining means 7 acquires the intensity distribution of light in a predetermined wavelength range relative to a pixel area that is specified by the pixel area specifying means, as shown in FIG. 13B.

Also, as shown in FIG. 13B for example, the fluorescent endoscope apparatus of the embodiment 1 is formed in such a way that, when a peak wavelength region of the fluorescence spectrum of a residue that is acquired by the intensity distribution acquiring member 7 relative to a pixel area specified through the pixel area specifying means is shifted from the peak wavelength region of the known fluorescence spectrum of the residue in the fluorescent image shown in FIG. 13A, the wavelength selection control adjusting means 8 automatically adjusts control of the wavelength selection and transmission means 2 selecting fluorescence detection wavelength region and transmitting light in the selected fluorescence detection wavelength region by the wavelength selection control means 4, in such a way that a fluorescence detection wavelength region $\lambda c$ corresponding to the fluorescence of the residue that is selected to be transmitted by the wavelength selection and transmission means 2 is shifted to a peak wavelength region $\lambda c'$ in the fluorescence spectrum of the residue that is acquired by the intensity distribution obtaining means 7.

In this case, the spectrum division means which is omitted in the drawings estimates the fluorescence spectrum of residue by the use of the known standard values of the spectrum of auto-fluorescence originating from the living body and the fluorescence spectrum of fluorescent agent and the use of a method of spectral estimation or UNMIXING, to separate the fluorescence spectrum of the residue from the fluorescence spectrum that is acquired by the intensity distribution obtaining means 7. In addition, the shift quantities of the fluorescence detection wavelength regions $\lambda$, $\lambda b$, and $\lambda c$ which correspond to the fluorescence components respectively are detected from peak values in the spectra of the respective fluorescence components which are separated from one another.

Embodiment 2

Figure 14A:
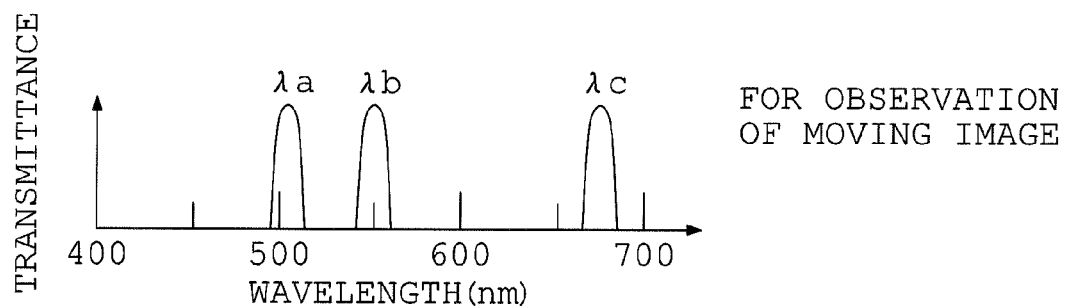
FIG. 14A is a view showing respective fluorescence detection wavelength regions.
Figure 14B:
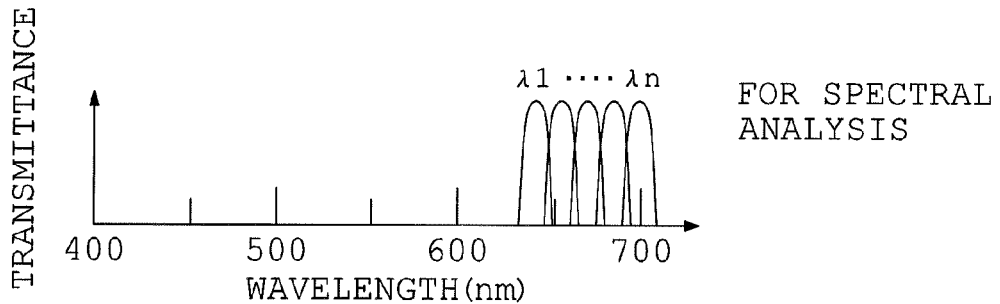
FIG. 14B is a view showing predetermined spectrum acquisition wavelength regions.
Figure 15:
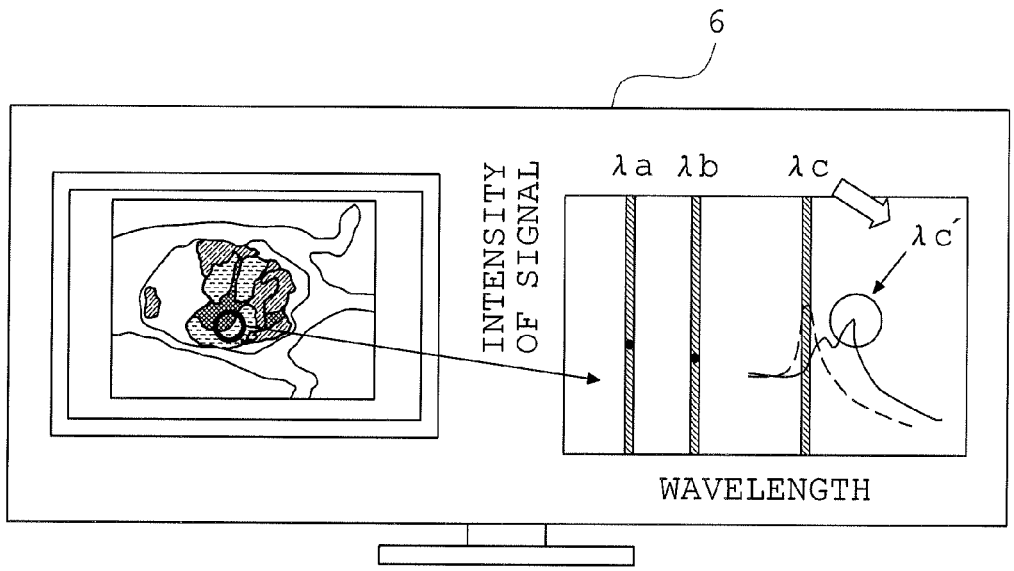
FIG. 15 is an explanatory view showing a fluorescence image which is displayed by the display means and showing a fluorescence spectrum which is acquired by the intensity distribution obtaining means, in the fluorescent endoscope apparatus of the embodiment 2, the left side of FIG. 15 is a view showing an image into which the images of light in three kinds of fluorescence detection wavelength regions that are written on respective frame memories for synthesis of fluorescence image are compounded by the fluorescent image compounding means and which is displayed by the image display means, and the right side of FIG. 15 is a view showing a state in which a peak wavelength region of the fluorescence spectrum of a residue that is acquired by the intensity distribution obtaining means relative to a pixel area specified through the pixel area specifying means is shifted from the peak wavelength region of a known fluorescence spectrum in the image that is displayed by the image display means.

FIG. 14 is a view showing one example of wavelength region which the wavelength selection and transmission means 2 selects to transmit light in the wavelength region in the fluorescent endoscope apparatus according to the embodiment 2, FIG. 14A is a view showing respective fluorescence detection wavelength regions, and FIG. 14B is a view showing predetermined spectrum acquisition wavelength regions. FIG. 15 is an explanatory view showing a fluorescence image which is displayed by the image display means 6 and showing a fluorescence spectrum which is acquired by the intensity distribution obtaining means 7, in the fluorescent endoscope apparatus of the embodiment 2, the left side of FIG. 15 shows an image into which the images of light in three kinds of fluorescence detection wavelength regions that are written on respective frame memories $13c_1$, $13c_2$, and $13c_3$ for synthesis of fluorescence image are combined by the fluorescent image compounding means 5 and which is displayed by the image display means 6, and the right side of FIG. 15 shows a state in which a peak wavelength region of the fluorescence spectrum of a residue that is acquired by the intensity distribution obtaining means 7 relative to a pixel area specified through the pixel area specifying means is shifted from the peak wavelength region of a known fluorescence spectrum in the image that is displayed by the image display means 6.

In the fluorescent endoscope apparatus of the embodiment 2, the wavelength selection control means 4 controls the wavelength selection and transmission means 2 in such a way that the wavelength selection and transmission means 2 selects: light in fluorescence detection wavelength regions $\lambda$, $\lambda b$, and $\lambda c$ which correspond to three kinds of fluorescence (auto-fluorescence, fluorescence emitting from fluorescent agent, and fluorescence emitting from feces that is a residue) that emit from three kinds of fluorescent agents that are shown in FIG. 8, respectively, as shown in FIG. 14; and light in spectrum acquisition wavelength regions $\lambda 1$, $\lambda 2$, $\lambda n$ which adjoin each other in turn with a predetermined wavelength width in a wavelength range of 630 to 705 nm that includes the fluorescence detection wavelength region $\lambda c$, to transmit the selected light.

Also, as shown in FIG. 15, the image display means 6 is formed in such a way that the image display means 6 displays the intensity distribution of light in a wavelength range of 630 to 705 nm which is acquired by the intensity distribution obtaining means 7, together with an image which is synthesized by the fluorescent image compounding means 5.

Also, the fluorescent endoscope apparatus of the embodiment 2 is formed in such a way that the wavelength selection control adjusting means 8 automatically adjusts control of the wavelength selection and transmission means 2 selecting fluorescence detection wavelength region and transmitting light in the selected fluorescence detection wavelength region by the wavelength selection control means 4, like the fluorescent endoscope apparatus of the embodiment 1. For example, as shown in the graph on the right side of FIG. 15, when a peak wavelength region $\lambda c'$ of the fluorescence spectrum of a residue that is acquired by the intensity distribution acquiring member 7 relative to a pixel area specified through the pixel area specifying means shifts from the peak wavelength region $\lambda c$ of the known fluorescence spectrum of the residue in the fluorescent image shown on the left side of FIG. 15, the wavelength selection control adjusting means 8 adjusts control of the wavelength selection and transmission means 2 selecting fluorescence detection wavelength region and transmitting light in the selected fluorescence detection wavelength region by the wavelength selection control means 4, in such a way that the fluorescence spectrum of the residue that is acquired by the intensity distribution fluorescence detection wavelength region corresponding to the fluorescence of the residue that is selected to be transmitted by the wavelength selection and transmission means 2 is shifted to the peak wavelength region $\lambda c'$ in the obtaining means 7.

As described above, in the case where the wavelength shift of only the residue should be noticed, the spectrum acquisition wavelength regions are limited to a wavelength range of 630 to 705 nm which includes the fluorescence detection wavelength region $\lambda c$, so that it is possible to reduce time to acquire spectrum, and it is possible to reduce drop frame of fluorescence image.

The other constitutions and operation effects of the fluorescent endoscope apparatus of the embodiment 2 are approximately the same as those of the fluorescent endoscope apparatus of the embodiment 1.

Embodiment 3

Figure 16A:
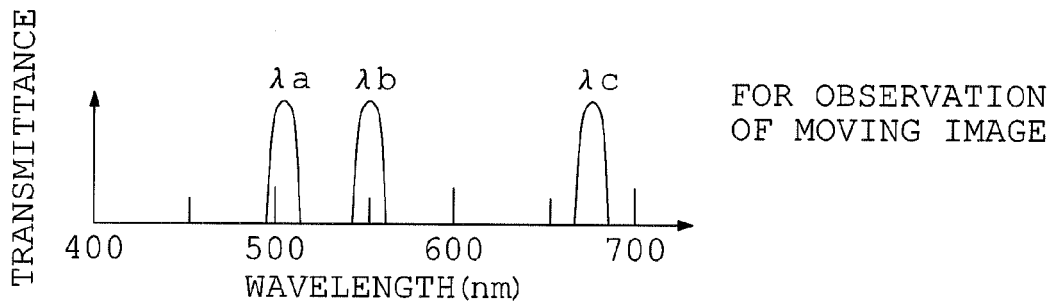
FIG. 16A is a view showing respective fluorescence detection wavelength regions.
Figure 16B:
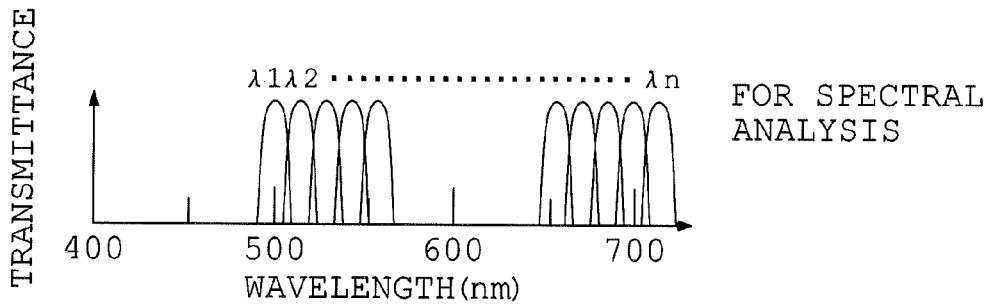
FIG. 16B is a view showing respective spectrum acquisition wavelength regions.

FIG. 16 is a view showing one example of wavelength region which the wavelength selection and transmission means 2 selects to transmit light in the wavelength region in the fluorescent endoscope apparatus according to the embodiment 3, FIG. 16A is a view showing respective fluorescence detection wavelength regions, and FIG. 16B is a view showing respective spectrum acquisition wavelength regions.

In the fluorescent endoscope apparatus of the embodiment 3, the wavelength selection control means 4 controls the wavelength selection and transmission means 2 in such a way that the wavelength selection and transmission means 2 selects: light in fluorescence detection wavelength regions λa, λb, and λc which correspond to three kinds of fluorescence (auto-fluorescence, fluorescence emitting from fluorescent agent, and fluorescence emitting from feces that is a residue) that emit from three kinds of fluorescent agents that are shown in FIG. 8, respectively, as shown in FIG. 16; and light in spectrum acquisition wavelength regions λ1, λ2, . . . , λn which adjoin each other in turn with a wavelength region in a wavelength band of 490 to 565 nm that includes the fluorescence detection wavelength regions λa and λb, or light in spectrum acquisition wavelength regions . . . , λn which adjoin each other in turn with a wavelength width in a wavelength range of 645 to 715 nm that includes the fluorescence detection wavelength region λc, to transmit the selected light.

Also, the fluorescent endoscope apparatus of the embodiment 3 is formed in such a way that the wavelength selection control adjusting means 8 manually adjusts control of the wavelength selection and transmission means 2 selecting fluorescence detection wavelength region and transmitting light in the selected fluorescence detection wavelength region by the wavelength selection control means 4. For example, as shown in the graph on the right side of FIG. 15, when a peak wavelength region λc' of the fluorescence spectrum of residue that is acquired by the intensity distribution acquiring member 7 relative to a pixel area specified through the pixel area specifying means shifts from the peak wavelength region λc of the known fluorescence spectrum of the residue in the fluorescent image shown on the left side of FIG. 15, an observer manually inputs a shift point on the screen (which is an area symbolized by λc' in the graph on the right side of FIG. 15) with keyboard or mouse which is not shown in the drawings, so that the wavelength selection control adjusting means 8 adjusts control of the wavelength selection and transmission means 2 selecting fluorescence detection wavelength region and transmitting light in the selected fluorescence detection wavelength region by the wavelength selection control means 4, in such a way that the fluorescence detection wavelength region corresponding to the fluorescence of the residue that is selected to be transmitted by the wavelength selection and transmission means 2 is shifted to a predetermined wavelength region that includes the peak wavelength region λc' in the fluorescence spectrum of the residue that is acquired by the intensity distribution obtaining means 7.

The other constitutions and operation effects of the fluorescent endoscope apparatus of the embodiment 3 are approximately the same as those of the fluorescent endoscope apparatus of the embodiment 2.

Embodiment 4

FIG. 17 is a view showing one example of wavelength region which the wavelength selection and transmission means 2 selects to transmit light in the wavelength region in the fluorescent endoscope apparatus according to the embodiment 4, and a view showing a state in which two kinds of fluorescence detection wavelength regions are shifted. FIG. 18 is an explanatory view showing a fluorescence image which is displayed by the image display means 6, showing a fluorescence spectrum which is acquired by the intensity distribution obtaining means 7, and showing the fluorescence spectrum which is divided by the spectrum division means, in the fluorescent endoscope apparatus of the embodiment 4, FIG. 18A is a view showing an image into which the images of light in three kinds of fluorescence detection wavelength regions that are written on respective frame memories $13c_1$, $13c_2$, and $13c_3$ for synthesis of fluorescence image are combined by the fluorescent image compounding means 5 and which is displayed by the image display means 6, FIG. 18B is a graph showing a fluorescence spectrum that is acquired by the intensity distribution obtaining means 7 relative to a pixel area specified through the pixel area specifying means in the image shown in FIG. 18A, and FIG. 18C is a graph showing the fluorescence spectrum shown in FIG. 18B which is divided into its fluorescence components by the spectrum division means.

In the fluorescent endoscope apparatus of the embodiment 4, wavelength regions which the wavelength selection and transmission means 2 selects to transmit light in the wavelength regions through the wavelength selection control means 4 are the same as those in the fluorescent endoscope apparatus of the embodiment 1 which are shown in FIGS. 11A and 11B. However, the fluorescent endoscope apparatus of the embodiment 4 is formed in such a way that, when not only a peak wavelength in the fluorescence spectrum of residue, but also a peak wavelength in the fluorescence spectrum of another fluorescence component due to the influence of factors except residue, such as bloodstream, (the spectrum of auto-fluorescence originating from a living body in the example of FIG. 17) shifts from the known peak wavelength, the wavelength selection control adjusting means 8 automatically adjusts control of the wavelength selection and transmission means 2 selecting fluorescence detection wavelength region and transmitting light in the selected fluorescence detection wavelength region by the wavelength selection control means 4, in such a way that a fluorescence detection wavelength region λc corresponding to the fluorescence of the residue that is selected to be transmitted by the wavelength selection and transmission means 2 and a fluorescence detection wavelength region λa corresponding to auto-fluorescence originating from the living body are shifted to a peak wavelength region λc' in the fluorescence spectrum of the residue and a peak wavelength region λa' in the auto-fluorescence spectrum originating from the living body that are acquired by the intensity distribution obtaining means 7, respectively.

Besides, as shown in FIG. 10, the fluorescent agent and residue also emit fluorescence with a relatively strong intensity in the vicinity of the peak wavelength region of auto-fluorescence originating from the living body. Accordingly, in the fluorescent endoscope apparatus of the embodiment 4, in order to detect the peak wavelength region of the spectrum of the auto-fluorescence with high precision, the spectrum division means (which is not shown in the drawings) divides into the fluorescence spectra of respective fluorescence components a fluorescence spectrum which is acquired by the intensity distribution obtaining means 7.

The spectrum division means separates the fluorescence spectra of a plurality of fluorescence components (fluorescence component originating from the living body, fluorescence component originating from fluorescent agent) from a fluorescence spectrum which is acquired by the intensity distribution obtaining means 7 relative to a pixel area that is specified by the pixel area specifying means in the fluorescence image shown in FIG. 18A (refer to FIG. 18B), for example. That is to say, a predetermined calculation is performed with methods such as spectral estimation and Unmixing that are described above, so that the fluorescence spectra of the respective fluorescence components are separated from one another.

And, when the peak wavelength in the fluorescence spectrum of the residue and the peak wavelength in the fluorescence spectrum of a fluorescence component originating from the living body shifts from the peak wavelengths in the respective known fluorescence spectra of the residue and the fluorescence components originating from the living body, respectively, in the peak wavelengths of the respective fluorescence spectra that are separated from one another, the wavelength selection control adjusting means 8 automatically adjusts control of the wavelength selection and transmission means 2 selecting fluorescence detection wavelength region and transmitting light in the selected fluorescence detection wavelength region by the wavelength selection control means 4, in such a way that the fluorescence detection wavelength region λc corresponding to the fluorescence of the residue and a fluorescence detection wavelength region λa corresponding to auto-fluorescence originating from the living body that are selected to be transmitted by the wavelength selection and transmission means 2 are shifted to the predetermined peak wavelength region λc' and the predetermined peak wavelength region λa', respectively, as described above.

Besides, in the fluorescent endoscope of the embodiment 4, it is possible to manually input and specify a region in which an observer desires to display spectrum through the pixel area specifying means, as in the fluorescent endoscope apparatus of the embodiment 1. However, the fluorescent endoscope apparatus of the embodiment 4 is formed in such a way that the acquisition and division of fluorescence spectrum and detection of peak wavelength region through the intensity distribution acquisition means 7, the spectrum division means, and so on, and the adjustment of control of the wavelength selection and transmission means 2 selecting fluorescence detection wavelength region and transmitting light in the selected fluorescence detection wavelength region by the wavelength selection control means 4 through the wavelength selection control means 8 (or, the shift of fluorescence detection wavelength region to a detected peak wavelength region) are automatically performed.

The other constitutions and operation effects of the fluorescent endoscope apparatus of the embodiment 4 are approximately the same as those of the fluorescent endoscope apparatus of the embodiment 1.

Besides, the fluorescent endoscope apparatus of the embodiment 4 may be formed in such a way that the image display means 6 is formed in such a way that the image display means 6 displays the intensity distributions of light of the respective fluorescence components into which a fluorescence spectrum that is acquired by the intensity distribution obtaining means 7 is divided by the spectrum division means, together with an image which is synthesized by the fluorescent image compounding means 5, as in the fluorescent endoscope apparatuses of the embodiments 2 and 3.

Also, in the fluorescent endoscope apparatus of embodiment 4, the wavelength selection control adjusting means 8 may be formed in such a way that control of the wavelength selection and transmission means 2 selecting fluorescence detection wavelength region and transmitting light in the selected fluorescence detection wavelength region by the wavelength selection control means 4 is manually adjusted (or, the adjustment is manually performed when the observer manually inputs a shift point for a peak wavelength region on the screen with keyboard or mouse which is not shown in the drawings), as in the fluorescent endoscope apparatus of the embodiment 3.

Embodiment 5

The fluorescent endoscope apparatus of the embodiment 5 may be formed in such a way that the image display means 6 is formed in such a way that the image display means 6 displays the intensity distribution of light of fluorescence components which is acquired by the intensity distribution obtaining means 7 and in which the fluorescence spectra of a plurality of the fluorescence components intermingle with one another, together with an image which is synthesized by the fluorescent image compounding means 5.

Besides, wavelength regions in the fluorescent endoscope apparatus of the embodiment 5 which the wavelength selection and transmission means 2 selects to transmit light in the wavelength regions through the wavelength selection control means 4 are the same as those in the fluorescent endoscope apparatus of the embodiment 1 which are shown in FIGS. 11A and 11B.

Also, in the fluorescent endoscope apparatus of embodiment 5, the wavelength selection control adjusting means 8 is formed in such a way that the control of the wavelength selection and transmission means 2 selecting fluorescence detection wavelength region and transmitting light in the selected fluorescence detection wavelength region by the wavelength selection control means 4 is manually adjusted (or, the adjustment is manually performed when the observer manually inputs a shift point for a peak wavelength region on the screen with keyboard or mouse which is not shown in the drawings), as in the fluorescent endoscope apparatus of the embodiment 3.

The other constitutions and operation effects of the fluorescent endoscope apparatus of the embodiment 5 are approximately the same as those of the fluorescent endoscope apparatus of the embodiment 3.

Embodiment 6

The fluorescent endoscope apparatus of the embodiment 6 is formed in such a way that all of the acquisition of fluorescence spectrum through the intensity distribution obtaining means 7, the division of the acquired fluorescence spectrum into the fluorescence spectra of its fluorescence components through the fluorescence spectrum division means, the extraction of peak wavelength regions in the fluorescence spectra of the respective fluorescence components through the wavelength selection control adjusting means 8, the calculations of the quantities of the shifts of the fluorescence detection wavelength regions to the peak wavelength regions, and the shifts of the fluorescence detection wavelength regions by the calculated shift quantities are automatically performed relative to each of pixels in an image that is displayed by the image display means 6.

Besides, the wavelength selection control adjusting means 8 determines a pixel area at which the adjustment to the shift to a fluorescence detection wavelength region that the wavelength selection and transmission means 2 selects to transmit light in the selected fluorescence detection wavelength region through control by the wavelength selection control means 4 is targeted, for example, in the following manner.

Figure 19A:
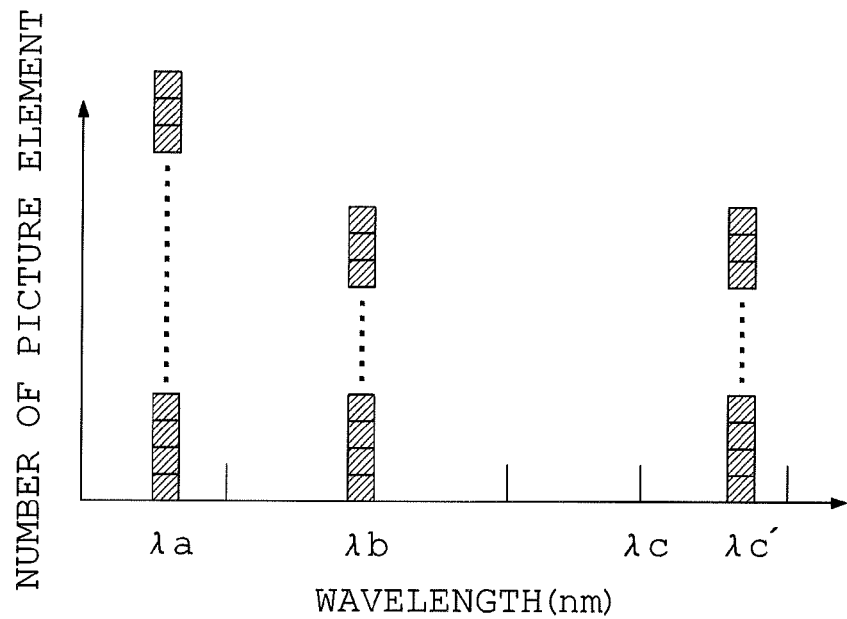
FIG. 19A is a view showing one example of wavelength region in which the brightness value becomes peak in the fluorescence spectrum of each of the fluorescence components into which the fluorescence spectrum that is acquired by the intensity distribution obtaining means is divided by the spectrum division means and showing one example of the number of pixels for each of the peak brightness values.
Figure 19B:
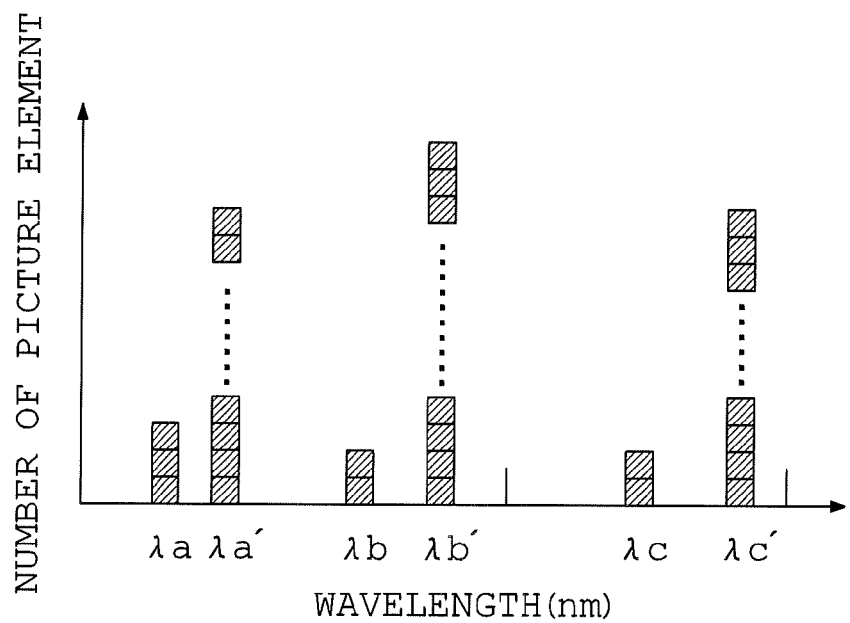
FIG. 19B is a view showing another example of wavelength region in which the brightness value becomes peak in the fluorescence spectrum of each of the fluorescence components into which the fluorescence spectrum that is acquired by the intensity distribution obtaining means is divided by the spectrum division means and showing another example of the number of pixels for each of the peak brightness values.

FIG. 19 is a view showing an example of a method for determining a pixel area which becomes an object for the adjustment to the shift to a fluorescence detection wavelength region which the wavelength selection and transmission means 2 selects to transmit light in the wavelength region by control from the wavelength selection control means 4 through the wavelength selection control adjusting means 8, in the fluorescent endoscope apparatus of the embodiment 6, FIG. 19A is a view showing one example of wavelength region in which the brightness value becomes peak in the fluorescence spectrum of each of the fluorescence components into which the fluorescence spectrum that is acquired by the intensity distribution obtaining means 7 is divided by the spectrum division means and showing one example of the number of pixels for each of the peak brightness values, and FIG. 19B is a view showing another example of wavelength region in which the brightness value becomes peak in the fluorescence spectrum of each of the fluorescence components into which the fluorescence spectrum that is acquired by the intensity distribution obtaining means 7 is divided by the spectrum division means and showing another example of the number of pixels for each of the peak brightness values.

When the brightness value in each of wavelengths in each of pixels is symbolized by Y, the brightness value Y is expressed by the following equation (5):

$$Y=f(\lambda) \tag{5}$$

Besides, because the wavelength selection and transmission means 2 selects an intensity distribution acquisition wavelength region with a predetermined wavelength width, to transmit light in the wavelength region, wavelength regions in which brightness value is not acquired could intermittently exist in a fluorescence spectrum which is acquired by the intensity distribution obtaining means 7. However, the brightness value in such a wavelength region can be supplemented by performing the spline interpolation or the like between wavelength regions in which the brightness values are acquired.

Also, both the brightness value of fluorescence spectrum which is acquired by the intensity distribution obtaining means 7 and in which its respective fluorescence components intermingle with one another and the brightness values of the fluorescent spectra of the fluorescence components which are separated from one another by the spectrum division means can be used as the brightness value Y.

A fluorescence spectrum has an extreme value in a wavelength region in which the brightness value becomes peak. Accordingly, the wavelength selection control adjusting means 8 calculates a wavelength region which has an extreme value of the fluorescence spectrum ($dy/d\lambda=df(\lambda)/d\lambda=0$), relative to a pixel area that an observer specifies through the pixel area specifying means or relative to all of the pixels.

Next, the wavelength selection control adjusting means 8 calculates the number of pixels z relative to each of wavelength regions in which the fluorescence spectrum of each of the fluorescence components has a maximal value as an extreme value. The number of pixels z can be expressed by the following equation (6):

$$z=g(\lambda) \tag{6}$$

In addition, the wavelength selection control adjusting means 8 calculates whether there exists a wavelength shift from the peak wavelength region in the known fluorescence spectra of the respective fluorescence components that become standards for the fluorescence spectra of the respective fluorescence components or not, and, in the case where there exists a wavelength shift in a fluorescence spectrum, the wavelength selection control means 8 calculates the shift quantity of the wavelength shift.

Next, the wavelength selection control adjusting means 8 determines a pixel area at which the adjustment to the shift of fluorescence detection wavelength region is targeted, by the use of threshold in the following manner as a first example.

When the total number of pixels is symbolized by So, the wavelength selection control adjusting means 8 adjusts control of the wavelength selection and transmission means 2 selecting fluorescence detection wavelength region and transmitting light in the selected fluorescence detection wavelength region by the wavelength selection control means 4, in such a way that: only when the number of pixels g ($\lambda c'$) for a wavelength region $\lambda c'$ in which the brightness value shown in FIG. 19A becomes a maximal value satisfies the following condition (7), the wavelength selection control adjusting means 8 chooses the pixel area for the wavelength region $\lambda c'$ as a pixel area at which the shift arrangement is targeted; and the fluorescence detection wavelength region is shifted from a predetermined wavelength region including the known wavelength region $\lambda c$ as a standard to a predetermined wavelength region including the wavelength region $\lambda c'$:

$$0.1 < g(\lambda)/So \tag{7}$$

Also, the wavelength selection control adjusting means 8 may determine a pixel area at which the adjustment to the shift of fluorescence detection wavelength region is targeted, in the following manner as a second example.

For example, the wavelength selection control adjusting means 8 adjusts control of the wavelength selection and transmission means 2 selecting fluorescence detection wavelength region and transmitting light in the selected fluorescence detection wavelength region by the wavelength selection control means 4, in such a way that: the wavelength selection control adjusting means 8 chooses only a peak wavelength region in which one of the numbers of pixels g ($\lambda c'$), g ($\lambda c'$), and g ($\lambda c'$) for respective wavelength regions $\lambda a'$ $\lambda b'$ and $\lambda c'$ which are shown in FIG. 19B satisfies the following condition (8a), (8b), or (8c) and the numbers of pixels of which exceeds the numbers of pixels g ($\lambda a$), g (kb), and g ($\lambda c$) for respective peak wavelength regions $\lambda$, $\lambda b$, and $\lambda c$ in the known fluorescence spectra of the respective fluorescence components that become standards for the fluorescence spectra of the respective fluorescence components, as a pixel area at which the shift arrangement is targeted; and the fluorescence detection wavelength region is shifted from a predetermined wavelength region including the known wavelength region $\lambda a$ ($\lambda b$, or $\lambda c$) as a standard to a predetermined wavelength region including the wavelength region $\lambda a'$ ($\lambda b'$, or $\lambda c'$):

$$g(\lambda a) < g(\lambda a') \tag{8a}$$

$$g(\lambda b) < g(\lambda b') \tag{8b}$$

$$g(\lambda c) < g(\lambda c') \tag{8c}$$

The other constitutions and operation effects of the fluorescent endoscope apparatus of the embodiment 6 are approximately the same as those of the fluorescent endoscope apparatus of the embodiment 4.

Besides, the fluorescent endoscope apparatus may be formed in such a way that the observer determines a pixel area at which the shift adjustment to fluorescence light detection wavelength region is targeted, by touching a remarkable area in a fluorescence image or by manually inputting the remarkably area using keyboard or mouse which is not shown in the drawings.

Also, in the embodiments 1 to 6, the fluorescence spectra of the three kinds of fluorescence components and fluorescence detection wavelength regions were explained. However, the number of fluorescence components and fluorescence detection wavelength regions in fluorescent endoscope apparatuses of the present invention are not limited to those in the fluorescent endoscope apparatuses of the embodiments 1 to 6, and fluorescent endoscope apparatuses of the present invention can deal with a constitution in which more fluorescence components and more fluorescence detection wavelength regions are used than those of the embodiments 1 to 6.

Also, the peak wavelength region of each of the three kinds of fluorescent agents which are used for the embodiments 1 to 6 is divided into R, G, and B wavelength regions. However, fluorescent endoscope apparatuses of the present invention are also applicable to observation by the use of plural kinds of fluorescent agents the peak wavelengths of which are present in one of the R, G, and B regions or in the near infrared region.

Also, the estimated value of a pixel in a wavelength range within a 20 nanometer radius of a wavelength that becomes an extreme value may be used as the number of pixels z in the above described equation (6).

Embodiment 7

Figure 20A:
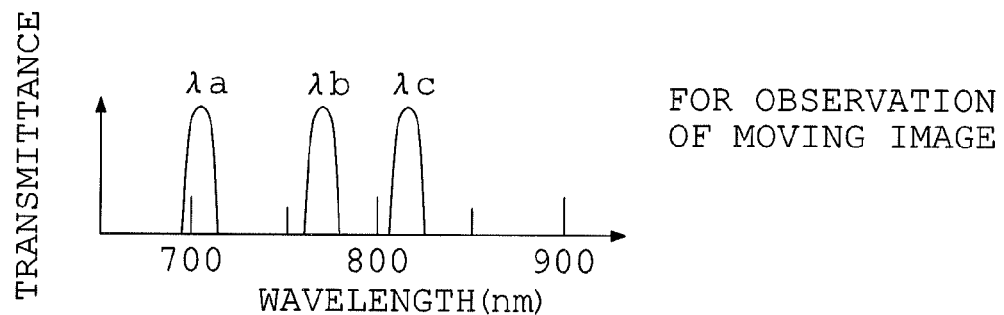
FIG. 20A is a view showing respective fluorescence detection wavelength regions.
Figure 20B:
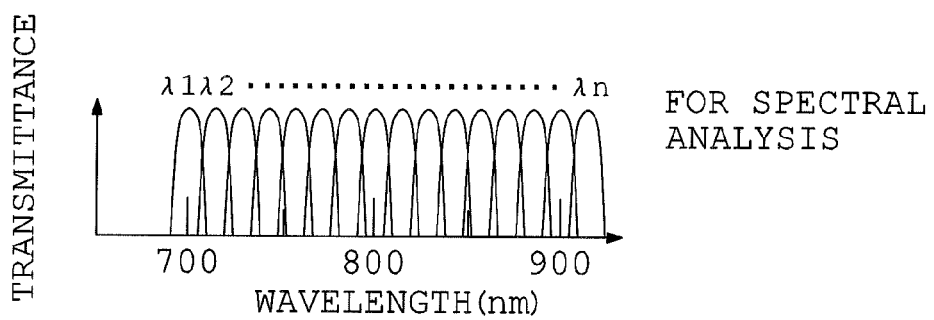
FIG. 20B is a view showing respective spectrum acquisition wavelength regions.
Figure 20C:
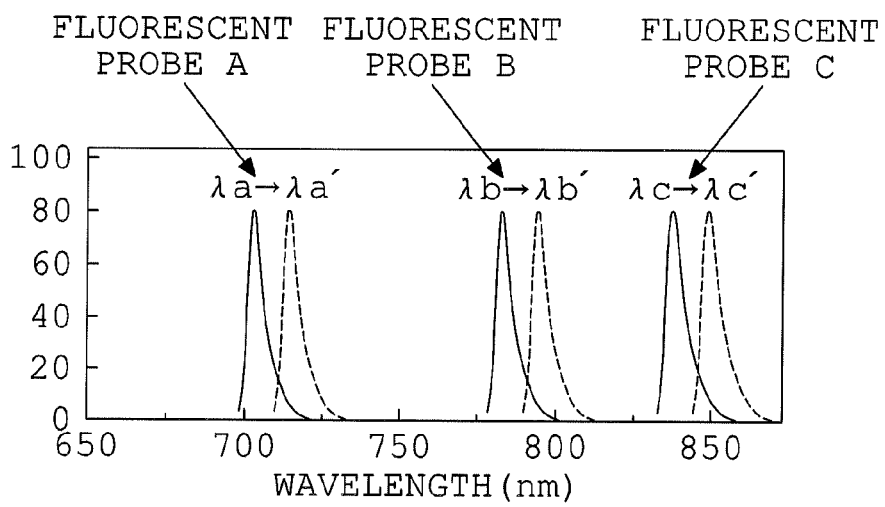
FIG. 20C is a graph showing a state the respective fluorescent spectra into which the fluorescence spectrum shown in FIG. 20B is divided as its fluorescence components by the spectrum division means are shifted from known fluorescence spectra, respectively.

FIG. 20 is a view showing one example of wavelength region which the wavelength selection and transmission means 2 selects to transmit light in the wavelength region in the fluorescent endoscope apparatus according to the embodiment 7, FIG. 20A is a view showing respective fluorescence detection wavelength regions, FIG. 20B is a view showing respective spectrum acquisition wavelength regions, and FIG. 20C is a graph showing a state the respective fluorescent spectra into which the fluorescence spectrum shown in FIG. 20B is divided as its fluorescence components by the spectrum division means are shifted from known fluorescence spectra, respectively.

The biological tissue 9 which is an object for observation in the fluorescent endoscope apparatus of the embodiment 7 is labeled with three kinds of fluorescent agents which emit fluorescence in a wavelength range of 700 to 720 nm, in a wavelength range of 755 to 800 nm, and in a wavelength range of 830 to 850 nm respectively, as a fluorescent probe, as shown in FIG. 20C, because excitation light in a wavelength range of less than 670 nm is radiated to the biological tissue 9. Besides, in the embodiment 7, it is optical characteristic of the excitation light cut filter $12b_3$ to block light in a wavelength range of 670 nm or less and to transmit light in the wavelength range of more than 670 nm.

The photo detector means 3 is composed of a monochrome CCD which is provided with a single chip image sensor (which is omitted in the drawings).

Also, in the fluorescent endoscope apparatus of the embodiment 7, the wavelength selection control means 4 controls the wavelength selection and transmission means 2 in such a way that the wavelength selection and transmission means 2 selects: light in fluorescence detection wavelength regions λa, λb, and λc which correspond to three kinds of fluorescence (fluorescence emitting from the three kinds of fluorescent agent) that emit from three kinds of fluorescent agents which are shown in FIG. 20C, respectively, as shown in FIGS. 20A and 20B; and light in spectrum acquisition wavelength regions λ1, λ2, . . . , λn which adjoin each other in turn with a wavelength width in a wavelength range of 690 to 915 nm that includes the fluorescence detection wavelength regions λa, λb, and λc, to transmit the selected light.

Also, the fluorescent endoscope apparatus of the embodiment 7 is formed in such a way that the wavelength selection control adjusting means 8 automatically adjusts control of the wavelength selection and transmission means 2 selecting fluorescence detection wavelength region and transmitting light in the selected fluorescence detection wavelength region by the wavelength selection control means 4, in such a way that the fluorescence detection wavelength regions λa, λb, and λc which correspond to fluorescences of the respective fluorescent agents into which the fluorescence spectrum that is acquired by the intensity distribution obtaining means 7 is divided by the spectrum division means to be selected to be transmitted by the wavelength selection and transmission means 2 are shifted to a predetermined wavelength regions λa', λb', and λc', respectively. The other constitutions and operation effects of the embodiment 7 are approximately the same as those of the fluorescent endoscope apparatus of one of the embodiments 1 to 6.

As is clear from the above described explanations, fluorescent endoscope apparatuses of the present invention are useful for fields in which fluorescence emitting from a living body is detected in order to observe the living body.

What is claimed is:

1. A fluorescent endoscope apparatus comprising:
an excitation light irradiation system configured to irradiate an observation area of a living body with excitation light for exciting plural kinds of fluorescent agents that exist in the observation area;
a wavelength-selective transmission member which selects and transmits light in predetermined wavelength regions out of incident light coming from the observation area of the living body;
a photodetector which photoelectrically converts the light that has been selected and transmitted by the wavelength-selective transmission member;
a wavelength selection control section which controls the wavelength-selective transmission member, to cause the wavelength-selective transmission member select and transmit light in fluorescence detection wavelength regions that correspond to plural kinds of florescence emitted from the plural kinds of fluorescent agents respectively and light in spectrum acquisition wavelength regions that serially adjoin each other at a predetermined wavelength width in a predetermined wavelength range that includes a fluorescence detection wavelength region corresponding to at least one kind of fluorescence in the plural kinds of fluorescence;
a fluorescence image synthesizer which synthesizes images of the light that has been selected and transmitted by the wavelength-selective transmission member and photoelectrically converted by the photodetector, in the fluorescence detection wavelength regions, to generate a synthesized image;
an image display device which displays at least the synthesized image generated by the fluorescence image synthesizer;
an intensity distribution acquisition section which acquires a peak wavelength region in an intensity distribution of light in the predetermined wavelength range by use of images of the light that has been selected and transmitted by the wavelength-selective transmission member and photoelectrically converted by the photodetector, in the respective spectrum acquisition wavelength regions in the predetermined wavelength range; and
a wavelength selection control adjusting section which adjusts control by the wavelength selection control section over the wavelength-selective transmission member regarding selection and transmission of fluorescence detection wavelength regions, in such a way that, when the peak wavelength region acquired by the intensity distribution acquisition section does not coincide with a fluorescence detection wavelength region that is selected to be transmitted by the wavelength-selective transmission member and that corresponds to the at least one kind of fluorescence, the fluorescence detection wavelength region is shifted to the peak wavelength region.

2. The fluorescent endoscope apparatus according to claim 1, wherein the wavelength selection control section controls the wavelength-selective transmission member in such a way that, after being made to select and transmit light in all of the fluorescence detection wavelength regions the wavelength-selective transmission member is made to select and transmit light in all of the spectrum acquisition wavelength regions.

3. The fluorescent endoscope apparatus according to claim 1, wherein the wavelength selection control section controls the wavelength-selective transmission member in such a way that, after being made to select and transmit light in all of the fluorescence detection wavelength regions, the wavelength-selective transmission member is made to select and transmit light in one of the spectrum acquisition wavelength regions, and that a sequence of these processes is repeated until selection and transmission of light in all of the spectrum acquisition wavelength regions is completed.

4. The fluorescent endoscope according to claim 1, wherein the wavelength selection control section has a first control mode in which control is made in such a way that the wavelength-selective transmission member is made to select and transmit light in all of the fluorescence detection wavelength regions, and a second control mode in which control is made in such a way that the wavelength-selective transmission member is made to select and transmit light in all of the spectrum acquisition wavelength regions, and
the wavelength selection control section is configured so that one of the first control mode and the second control mode can be actuated via a manual selection.

5. The fluorescent endoscope apparatus according to claim 1, wherein the wavelength selection control section has a first control mode in which control is made in such a way that the wavelength-selective transmission member is made to select and transmit light in all of the fluorescence detection wavelength regions, and a third control mode in which control is made in such a way that, after being made to select and transmit light in all of the fluorescence detection wavelength regions, the wavelength-selective transmission member is made to select and transmit light in one of the spectrum acquisition wavelength regions and that a sequence of these processes is repeated until selection and transmission of light in all of the spectrum acquisition wavelength regions is completed, and
the wavelength selection control section is configured so that one of the first control mode and the third control mode can be actuated via a manual selection.

6. The fluorescent endoscope apparatus according to claim 1, wherein the fluorescent endoscope apparatus further comprises a pixel area specifying section which specifies a desired pixel area for which the intensity distribution of light in the predetermined wavelength range is acquired by the intensity distribution acquisition section, and
the light intensity distribution acquisition section acquires the intensity distribution of light in the predetermined wavelength range for a pixel area that is specified by the pixel area specifying section.

7. The fluorescent endoscope apparatus according to claim 1, wherein the wavelength selection control adjusting section automatically makes an adjustment to control by the wavelength selection control section over the wavelength-selective transmission member regarding selection and transmission of the fluorescence detection wavelength regions.

8. The fluorescent endoscope apparatus according to claim 1, wherein the wavelength selection control adjusting section manually makes an adjustment to control by the wavelength selection control section over the wavelength-selective transmission member regarding selection and transmission of the fluorescence detection wavelength regions.

9. The fluorescent endoscope apparatus according to claim 1, wherein the fluorescent endoscope apparatus further comprises a moving amount detector which detects a moving amount in the observation area by using a change of a fluorescence image which is a synthesized image generated by the fluorescence image synthesizer,
the wavelength selection control section has a first control mode in which control is made in such a way that the wavelength-selective transmission member is made to select and transmit light in all of the fluorescence detection wavelength regions, and a second control mode in which control is made in such a way that the wavelength-selective transmission is made to select and transmit light in all of the spectrum acquisition wavelength regions, and
the wavelength selection control section is configured so that, when the moving amount detected by the moving amount detector is equal to or smaller than a predetermined value, the second control mode is actuated, and so that, when the moving amount detected by the moving amount detector is larger than the predetermined value, the first control mode is actuated.

10. The fluorescent endoscope apparatus according to claim 9, wherein the intensity distribution acquisition section operates when the moving amount detected by the moving amount detector is equal to or smaller than the predetermined value.

11. The fluorescent endoscope apparatus according to claim 1, wherein the fluorescent endoscope apparatus further comprises a moving amount detector which detects a moving amount in the observation area by using a change of a fluorescence image which is a synthesized image generated by the fluorescence image synthesizer,
the wavelength selection control section has a first control mode in which control is made in such a way that the wavelength-selective transmission member is made to select and transmit light in all of the fluorescence detection wavelength regions, and a third control mode in which control is made in such a way that, after being made to select and transmit light in all of the fluorescence detection wavelength regions, the wavelength-selective transmission member is made to select and transmit light in one of the spectrum acquisition wavelength regions and that a sequence of these processes is repeated until selection and transmission of light in all of the spectrum acquisition wavelength regions is transmitted completed, and
the wavelength selection control section is configured so that, when the moving amount detected by the moving amount detector is equal to or smaller than a predetermined value, the third control mode is actuated, and so that, when the moving amount detected by the moving amount detector is larger than the predetermined value, the first control mode is actuated.

12. The fluorescent endoscope apparatus according to claim 11, wherein the intensity distribution acquisition section operates when the moving amount detected by the moving amount detector is equal to or smaller than the predetermined value.

13. The fluorescent endoscope apparatus according to claim 1, wherein the fluorescent endoscope apparatus further comprises a moving amount detector which detects a moving amount in the observation area by using a change of a fluorescence image which is a synthesized image generated by the fluorescence image synthesizer, and the intensity distribution acquisition section operates when the moving amount detected by the moving amount detector is equal to or smaller than a predetermined value.

14. The fluorescent endoscope apparatus according to claim 1, wherein the fluorescent endoscope apparatus further comprises a target wavelength range setting section which sets, as the predetermined wavelength range, a target wavelength range in which the intensity distribution acquiring section acquires the intensity distribution of light.

15. The fluorescent endoscope apparatus according to claim 1, wherein the fluorescent endoscope apparatus further comprises a spectrum separating section which separates out a specific spectrum by using the intensity distribution of light in the predetermined wavelength range acquired by the intensity distribution acquisition section.

16. The fluorescent endoscope apparatus according to claim 1, wherein the image display device displays the intensity distribution of light in the predetermined wavelength range which is acquired by the intensity distribution acquisition section, together with a synthesized image which is generated by the fluorescence image synthesizer.

\* \* \* \* \*